US012685653B2

(12) United States Patent
Schreck

(10) Patent No.: US 12,685,653 B2
(45) Date of Patent: Jul. 21, 2026

(54) DEVICES AND METHODS FOR TREATING BIFURCATING BLOOD VESSELS

(71) Applicant: Restore Endosystems, LLC, Trabuco Canyon, CA (US)

(72) Inventor: Stefan Georg Schreck, Duvall, WA (US)

(73) Assignee: Restore Endosystems, LLC, Trabuco Canyon, CA (US)

( * ) Notice: Subject to any disclaimer, the term of this patent is extended or adjusted under 35 U.S.C. 154(b) by 636 days.

(21) Appl. No.: 18/177,027

(22) Filed: Mar. 1, 2023

(65) Prior Publication Data

US 2023/0210679 A1 Jul. 6, 2023

Related U.S. Application Data

(63) Continuation of application No. PCT/US2021/050688, filed on Sep. 16, 2021.

(60) Provisional application No. 63/079,276, filed on Sep. 16, 2020.

(51) Int. Cl.
*A61F 2/954* (2013.01)
*A61F 2/958* (2013.01)
*A61M 25/10* (2013.01)
*A61F 2/06* (2013.01)

(52) U.S. Cl.
CPC .............. *A61F 2/954* (2013.01); *A61F 2/958* (2013.01); *A61F 2002/065* (2013.01); *A61F 2230/0006* (2013.01); *A61F 2230/0008* (2013.01); *A61M 2025/1013* (2013.01); *A61M 2025/1045* (2013.01)

(58) Field of Classification Search
CPC ............ A61F 2/07; A61F 2/954; A61F 2/958; A61M 25/1011; A61M 25/1045
See application file for complete search history.

(56) References Cited

U.S. PATENT DOCUMENTS

| | | | |
|---|---|---|---|
| 5,824,055 A | 10/1998 | Spiridigliozzi et al. | |
| 6,017,324 A | 1/2000 | Tu et al. | |
| 6,045,557 A | 4/2000 | White et al. | |
| 6,086,611 A * | 7/2000 | Duffy ........................ | A61F 2/82 |
| | | | 623/1.35 |

(Continued)

FOREIGN PATENT DOCUMENTS

| | | |
|---|---|---|
| CN | 102470029 A | 5/2012 |
| EP | 0965311 A2 | 12/1999 |

(Continued)

OTHER PUBLICATIONS

Partial European Search Report dated Sep. 25, 2024 for EP21878652.3.

(Continued)

*Primary Examiner* — Sarah W Aleman
(74) *Attorney, Agent, or Firm* — Dorsey & Whitney LLP

(57) ABSTRACT

Medical devices and methods for placing a bifurcated stent into a bifurcating blood vessel are described herein. Also, described herein are methods for treating aorto-iliac occlusive disease. The bifurcated stent can be mounted onto a catheter comprising at least two balloons by mounting a first branch stent of the bifurcated stent onto a first balloon and a second branch stent of the bifurcated stent onto a second balloon, and a main body of the bifurcated stent onto the first balloon and second balloon.

20 Claims, 40 Drawing Sheets

(56) References Cited

U.S. PATENT DOCUMENTS

| | | | | |
|---|---|---|---|---|
| 6,099,497 | A * | 8/2000 | Adams | A61F 2/958 604/103.05 |
| 6,165,195 | A | 12/2000 | Wilson | |
| 6,355,061 | B1 | 3/2002 | Quiachon et al. | |
| 6,537,284 | B1 * | 3/2003 | Inoue | A61F 2/954 623/1.11 |
| 6,558,396 | B1 * | 5/2003 | Inoue | A61F 2/954 623/1.11 |
| 7,959,667 | B2 | 6/2011 | Ta et al. | |
| 8,257,431 | B2 | 9/2012 | Henderson et al. | |
| 9,539,083 | B2 | 1/2017 | Krimsky et al. | |
| 10,219,926 | B2 | 3/2019 | Bourang et al. | |
| 2002/0077692 | A1 * | 6/2002 | Besselink | A61F 2/86 623/1.12 |
| 2004/0049204 | A1 | 3/2004 | Harari et al. | |
| 2004/0127850 | A1 * | 7/2004 | Steadham | A61M 25/10 604/103 |
| 2004/0148007 | A1 | 7/2004 | Jackson et al. | |
| 2004/0176837 | A1 * | 9/2004 | Atladottir | A61F 2/958 623/1.2 |
| 2004/0200978 | A1 | 10/2004 | Kamijo | |
| 2005/0043784 | A1 | 2/2005 | Yampolsky et al. | |
| 2005/0149168 | A1 | 7/2005 | Gregorich | |
| 2005/0192656 | A1 * | 9/2005 | Eidenschink | A61F 2/958 623/1.11 |
| 2005/0228472 | A1 | 10/2005 | Case et al. | |
| 2006/0212113 | A1 | 9/2006 | Shaolian et al. | |
| 2007/0142819 | A1 | 6/2007 | El-nounou et al. | |
| 2007/0168020 | A1 | 7/2007 | Brucker et al. | |
| 2007/0213802 | A1 | 9/2007 | Von et al. | |
| 2007/0270769 | A1 | 11/2007 | Wilson et al. | |
| 2007/0299495 | A1 | 12/2007 | Zukowski et al. | |
| 2008/0051869 | A1 | 2/2008 | Yribarren | |
| 2008/0103587 | A1 | 5/2008 | Henderson et al. | |
| 2008/0114438 | A1 * | 5/2008 | Hartley | A61F 2/954 623/1.11 |
| 2008/0125847 | A1 | 5/2008 | Krever et al. | |
| 2008/0133000 | A1 | 6/2008 | Molony | |
| 2009/0012601 | A1 * | 1/2009 | Siu | A61F 2/958 623/1.35 |
| 2009/0124968 | A1 | 5/2009 | Goshgarian | |
| 2009/0204083 | A1 | 8/2009 | Odonnell et al. | |
| 2009/0259288 | A1 | 10/2009 | Wijay et al. | |
| 2009/0259293 | A1 | 10/2009 | Moloney | |
| 2009/0299453 | A1 | 12/2009 | Arcand et al. | |
| 2010/0106238 | A1 | 4/2010 | Hilaire et al. | |
| 2011/0208286 | A1 | 8/2011 | Ta et al. | |
| 2013/0053940 | A1 | 2/2013 | Suhr | |
| 2013/0123907 | A1 * | 5/2013 | Roeder | A61F 2/958 623/1.23 |
| 2013/0296997 | A1 | 11/2013 | Kamat | |
| 2014/0214002 | A1 | 7/2014 | Lieber et al. | |
| 2014/0277353 | A1 | 9/2014 | Hartley | |
| 2014/0324150 | A1 * | 10/2014 | Stephens | A61F 2/07 623/1.11 |
| 2015/0126986 | A1 | 5/2015 | Kelly et al. | |
| 2015/0250579 | A1 | 9/2015 | Howard et al. | |
| 2015/0289875 | A1 | 10/2015 | Consigny et al. | |
| 2017/0007431 | A1 | 1/2017 | Al-Saadon | |
| 2018/0015264 | A1 | 1/2018 | Wang et al. | |
| 2020/0375724 | A1 | 12/2020 | Perkins et al. | |
| 2021/0401566 | A1 * | 12/2021 | Geusen | A61F 2/07 |
| 2022/0077692 | A1 | 3/2022 | Myers et al. | |
| 2022/0387200 | A1 * | 12/2022 | Kamat | A61F 2/954 |
| 2023/0144448 | A1 | 5/2023 | Schreck | |
| 2023/0146392 | A1 | 5/2023 | Mottola et al. | |
| 2024/0156622 | A1 | 5/2024 | Hall et al. | |
| 2024/0156627 | A1 | 5/2024 | Adams et al. | |

FOREIGN PATENT DOCUMENTS

| | | |
|---|---|---|
| EP | 1920734 A2 | 5/2008 |
| EP | 2068761 B1 | 2/2019 |
| JP | 2003502080 A | 1/2003 |
| WO | 2000027307 | 5/2000 |
| WO | 0143665 A2 | 6/2001 |
| WO | 2009131309 A2 | 10/2009 |
| WO | 2022060994 A1 | 3/2022 |

OTHER PUBLICATIONS

European Search Report dated Aug. 22, 2024 for EP21870220.7.
European Search Report dated Dec. 16, 2024 for EP21878652.3.
International Search Report and Written Opinion dated Mar. 20, 2024 for PCT/US2023/079678.
International Search Report and Written Opinion dated Apr. 24, 2024 for PCT/US2023/079627.
International Search Report and Written Opinion dated Jan. 14, 2022 for PCT/US2021/054258.
International Search Report and Written Opinion dated Feb. 4, 2022 for PCT/US2021/050688.
International Search Report and Written Opinion dated Apr. 19, 2023 for PCT/US2022/081847.
Extended European Search Report dated Sep. 24, 2025 for EP22908768.9.
Office Action dated Oct. 14, 2025 for U.S. Appl. No. 18/067,321.
Office Action dated Jan. 28, 2026 for U.S. Appl. No. 17/929,260.
Office Action dated Mar. 11, 2026 for U.S. Appl. No. 18/508,539.
Notice of Allowance dated Mar. 25, 2026 for U.S. Appl. No. 18/067,321.
Office Action dated Mar. 24, 2026 for U.S. Appl. No. 18/509,005.
Notice of Allowance dated May 12, 2026 for U.S. Appl. No. 17/929,260.

* cited by examiner 701a
701b
701c
701d 702a
702b
702c
702d
702d

DEVICES AND METHODS FOR TREATING BIFURCATING BLOOD VESSELS

CROSS REFERENCE TO RELATED APPLICATION

This application is a continuation of PCT/US2021/ 050688, filed Sep. 16, 2021, titled, "DEVICES AND METHODS FOR TREATING BIFURCATING BLOOD VESSELS", which claims the benefit of U.S. Provisional Patent Application Ser. No. 63/079,276, filed Sep. 16, 2020, the entire disclosure of each is incorporated herein by reference.

TECHNICAL FIELD

Medical devices and methods for placing a bifurcated stent into a bifurcating blood vessel are described herein. Also, described herein are methods for treating aorto-iliac occlusive disease.

BACKGROUND

Aorto-iliac occlusive disease (AIOD) refers to narrowing or stenosis of the blood vessels involving the infra-renal aorta and the two iliac arteries. In complex cases of AIOD, the aorto-iliac bifurcation can be involved.

Placement of a bare or covered stent is one method of treating local narrowing or occlusions of arteries. The stent can be self-expanding or balloon expandable. The "kissing-stent" technique and the covered endovascular reconstruction of aortic bifurcation (CERAB) technique have been developed to treat AOID involving the aorto-iliac bifurcation. Both include simultaneous placement of two parallel or "kissing" stents across the bifurcation. A shortcoming of these two techniques is the disruption of the natural blood flow through the bifurcation that can lead to thrombose formation, hemolysis, emboli and restenosis. Another shortcoming is the need for accurate simultaneous placement of the two kissing stents. Yet another shortcoming is the high technical skill set required to perform this procedure. Further yet, another shortcoming is that the two kissing stents make re-intervention procedures using a retrograde approach (up-and-over technique) very challenging.

As an alternative approach, self-expanding bifurcated stent grafts (AFX device manufactured by Endologix) have been used to treat complex aorto-iliac disease. The advantage of the bifurcated stent graft is that it preserves the bifurcation avoiding flow disturbances and allowing for a retrograde approach for re-intervention. However, a shortcoming to this approach is that the self-expanding stent can have insufficient outward force to maintain a patent flow lumen. Another shortcoming is the diameter of the delivery system. Yet another shortcoming is the complex procedural steps and high technical skill set that is required to place the bifurcated stent graft in the aorto-iliac bifurcation.

There is an obvious need for medical devices and methods for the treatment of AIOD involving the aorto-iliac bifurcation that overcome the above listed shortcomings of existing methods. The medical devices and methods for the treatment of AIOD involving the aorto-iliac bifurcation described herein fulfill that need.

BRIEF SUMMARY

Described herein generally are devices and methods for the treatment of any disease involving a bifurcation in a body lumen. In some embodiments, the devices and methods are for the treatment of aorto-iliac occlusive disease (AOID). In other embodiments, the devices and methods are for the treatment of AOID, particularly occlusive disease involving the aorto-iliac bifurcation. The devices can be introduced percutaneously or by surgical cutdown into a patient. The devices and methods described herein can also be used for the treatment of an aortic aneurysm or any other disease(s) in the body involving a bifurcation in a body lumen. In some embodiments, the device is a medical device. In other embodiments, the devices are bifurcated stents.

For consistency, when describing the present devices the direction toward the external end of the catheter outside the body is referred to as "proximal" and the direction away from the external end of the catheter is referred to as "distal". The side on which the catheter is inserted into peripheral arteries is referred to as "ipsi-lateral", the opposite side is referred to as "contralateral". For example, if the catheter is inserted into an artery of the right leg, the right side of the body is referred to as ipsi-lateral and the right iliac artery is referred to as the ipsi-lateral iliac artery. The left side is referred to as contra-lateral and the left iliac artery is referred to as the contra-lateral iliac artery.

In some embodiments, a bifurcated stent comprises a main body stent and at least two branch stents. In other embodiments, a bifurcated stent comprises a main body stent, at least two branch stents, and a catheter. The catheter can be configured to place the bifurcated stent into the aorto-iliac bifurcation. In some embodiments, the bifurcated stent can comprise more than two branch stents.

In other embodiments, the bifurcated stent comprises a tubular stent forming a main body and at least two tubular stents forming at least two branches. In some embodiments, the bifurcated stent comprises more than two tubular stents forming more than two branches.

The bifurcated stent can be a bare metal stent. In other embodiments, the bifurcated stent can be a covered stent. The stent can be composed of a metal, a polymer, and/or a combination thereof. The stent cover can be made from a polymer or mammalian tissue. The bifurcated stent can comprise a series of stent rings connected by longitudinal struts.

In some embodiments, the stent can be laser cut from a metal tube. In other embodiments, the stent can be formed from a metal wire. In some embodiments, the main body stent and the two branch stents can be welded together or connected by another mechanism, such as but not limited to, suture(s), adhesive(s), connector(s) and/or a combination thereof. In some embodiments, the main body stent and two branch stents are connected by a material different than the material used to compose the stents. The bifurcated stent can comprise a series of individual stent rings connected by the cover. The bifurcated stent can comprise at least two overlapping stents wherein the proximal segment of each stent forms a respective branch and the distal segment of each stent forms the main body. In some embodiments, the bifurcated stent comprises two or more overlapping stents.

In some embodiments, the catheter includes a catheter shaft and at least two balloons. In other embodiments, the catheter includes a catheter shaft and two or more balloons. In some embodiments, the catheter includes a catheter shaft and at least two balloons, a first balloon and a second balloon that are mounted onto the catheter shaft. The catheter can have a flexible segment between the first balloon and the second balloon. In some embodiments, where the catheter includes more than two balloons there can also be more than one flexible segment included. The flexible segment can be configured to allow the catheter shaft to be folded onto itself such that the at least two balloons are substantially parallel to each other. The catheter can have a first configuration in which the at least two balloons are substantially parallel to each other. In other embodiments, the catheter can have a second configuration in which the at least two balloons are substantially in series.

The catheter shaft can include an inflation lumen in fluid communication with a hub at the proximal end of the shaft (external to the patient's body) and in fluid communication with the at least two balloons.

In some embodiments, the catheter shaft can include a first opening at the proximal end of the catheter and a second opening along the catheter shaft between the at least two balloons. A lumen can connect the two openings, whereby the lumen provides a passageway for a first guidewire. In other embodiments, the catheter can include a first opening at the proximal end of the catheter and a second opening distal to the second balloon. A lumen can connect the two openings, whereby the lumen provides a passageway for a second guidewire.

In some embodiments, the catheter can be configured at the distal end of the catheter to snare the catheter. The catheter can be configured by the use of a hook(s), antenna(s), or extension(s) of any geometry that facilitates the placement of a loop of the snare over the distal end of the catheter.

The balloons described herein can be any shape. In some embodiments, the balloons can be of a cylindrical shape. In other embodiments, the balloons can include at least one local narrowing to increase the flexibility of the balloon when inflated. In some embodiments, the balloons can comprise an array (at least two) of smaller balloons mounted in series with flexible sections between the individual balloons. The balloons can have a proximal segment including a first diameter and a distal segment including a second diameter. In some embodiments, the first diameter is smaller than the second diameter. In other embodiments, the first diameter is larger than the second diameter. In some embodiments, the first diameter and the second diameter are the same.

The bifurcated stent can be mounted onto a catheter comprising at least two balloons by mounting a first branch stent of the bifurcated stent onto a first balloon and a second branch stent of the bifurcated stent onto a second balloon, and a main body of the bifurcated stent onto the first balloon and second balloon.

Methods of placing a bifurcated stent into the aorto-iliac bifurcation are also described herein. The methods can utilize the bifurcated stents and catheters described herein.

In other embodiments, the method for placing a bifurcated stent into the aorto-iliac bifurcation of a patient comprises: a) mounting a first branch stent of a bifurcated stent onto a first balloon and a second branch stent of the bifurcated stent onto a second balloon, and a main body stent of the bifurcated stent onto both the first balloon and second balloon; b) advancing a first guidewire from an ipsi-lateral leg artery through an ipsi-lateral iliac artery into the aorta; c) inserting a proximal end of a guidewire into a distal opening of a first guidewire lumen; d) advancing a catheter with the stent mounted onto the balloons over the first guidewire past the aorto-iliac bifurcation into the aorta; e) advancing a snare from a contra-lateral leg artery to a distal end of the catheter; f) snaring the distal end of the catheter; g) placing the bifurcated stent onto the aorto-iliac bifurcation by partially retracting the catheter on the ipsi-lateral side and partially retracting the snare holding the distal end of the catheter on the contra-lateral side; h) injecting fluid into an inflation lumen thereby inflating the balloons and expanding the bifurcated stent; i) withdrawing the fluid from the inflation lumen and collapsing the balloons; j) releasing the tip of the catheter from the snare; k) retracting the catheter through the ipsi-lateral iliac artery, and l) removing the catheter from the patient.

If needed, post-ballooning of the bifurcated stent can be performed to conform the main body stent and the at least two branch stents to the vessel wall of the aorta and iliac arteries, respectively. The sequence of steps can be altered, some steps can be removed, and/or additional steps can be performed. The same steps or similar steps can be used to treat other bifurcations in the body.

In some embodiments, the patient is a mammal. In other embodiments, the mammal is human.

In other embodiments, a method of placing a bifurcated stent in a patient comprises: a) mounting a first branch stent of the bifurcated stent onto a first balloon and a second branch stent of the bifurcated stent onto a second balloon, and the main body stent of the bifurcated stent onto both the first balloon and second balloon; b) advancing a first guidewire from a leg artery through the ipsi-lateral iliac artery into the aorta; c) inserting a proximal end of a first guidewire into a distal end of a first guidewire lumen; d) advancing a catheter with the bifurcated stent mounted onto the balloons over the first guidewire past the aorto-iliac bifurcation into the aorta; e) inserting a distal end of a second guidewire into a proximal opening of the second guidewire lumen; f) advancing the second guidewire through the second guidewire lumen into the contralateral iliac artery; g) placing the bifurcated stent onto the aorto-iliac bifurcation by partially retracting the catheter on the ipsi-lateral side; h) injecting fluid into an inflation lumen thereby inflating the balloons and expanding the bifurcated stent; i) withdrawing the fluid from the inflation lumen and collapsing the balloons; j) retracting the second guidewire from the catheter; k) retracting the catheter through the ipsi-lateral iliac artery, l) removing the catheter from the patient.

If needed, post-ballooning of the bifurcated stent can be performed to conform the main body stent and the two branch stents to the vessel wall of the aorta and iliac arteries, respectively. The sequence of steps can be altered, steps can be removed, and/or additional steps can be performed. The same steps or similar steps can be used to treat other bifurcations in the body.

In some embodiments, a snare can be advanced from the contra-lateral side to capture the second guidewire and facilitate the placement of the second guidewire into the contra-lateral iliac artery. In other embodiments, a guide catheter can be placed into the ipsi-lateral iliac artery or the aorta. The catheter can be advanced through the guide catheter. In some embodiments, the second guidewire is not removed but stays in place in the contra-lateral iliac artery to facilitate additional procedures involving the contra-lateral arteries.

BRIEF DESCRIPTION OF DRAWINGS

FIG. 18A illustrates a cross-sectional view of an embodiment of a bifurcated stent system as described herein.

FIG. 18B illustrates a cross-sectional view of an embodiment of a bifurcated stent system as described herein.

FIG. 20B illustrates capturing a distal end of a distal shaft of bifurcated stent system of FIG. 20A with a intravascular snare.

FIG. 20C illustrates retracting the bifurcated stent system of FIG. 20A onto an aorto-iliac bifurcation.

FIG. 20D illustrates inflating balloons of the bifurcated stent system of FIG. 20A to expand a bifurcated stent.

FIG. 20E illustrates deflating balloons of the bifurcated stent system of FIG. 20A.

FIG. 20F illustrates releasing a distal shaft of bifurcated stent system of FIG. 20A from the intravascular snare.

FIG. 20G illustrates withdrawing a catheter of the bifurcated stent system of FIG. 20A from an atrial system.

FIG. 21C illustrates retracting the bifurcated stent system of FIG. 21A onto a aorta-iliac bifurcation.

FIG. 21D illustrates inflating balloons of the bifurcated stent system of FIG. 21A.

FIG. 21E illustrates deflating the balloons of the bifurcated stent system of FIG. 21A.

FIG. 21G illustrates withdrawing a catheter of the bifurcated stent system of FIG. 21A.

DETAILED DESCRIPTION

Figure 1:
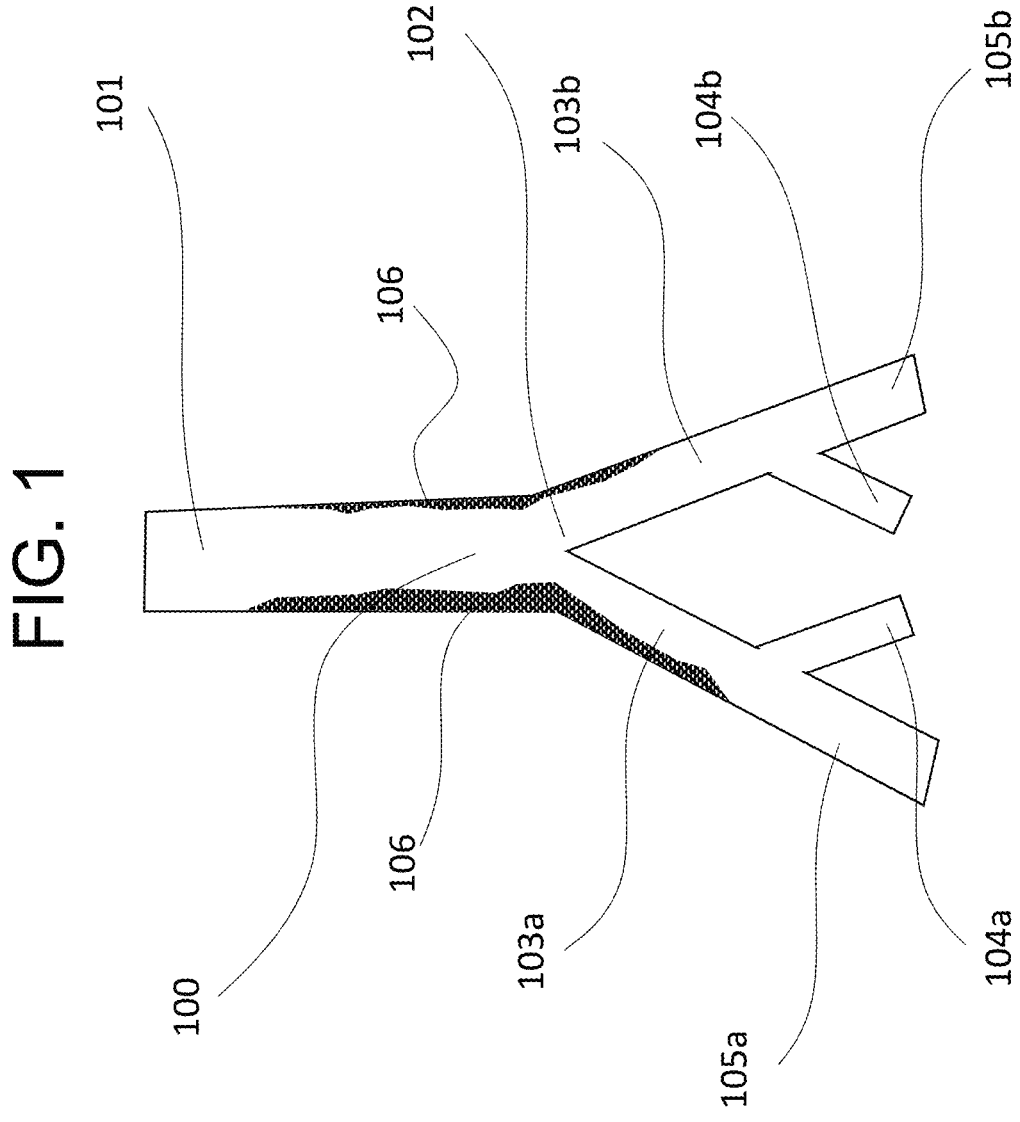
FIG. 1 illustrates the anatomy of an aorto-iliac bifurcation.

FIG. 1 illustrates the anatomy of aorto-iliac arteries (100). Infra-renal aorta (101) branches at aorto-iliac bifurcation (102) into two common iliac arteries (103a-b), each common iliac artery (103a-b) branches in external iliac artery (104a-b) and internal iliac artery (105a-b).

The dimensions of aorto-iliac bifurcation (102) can vary from patient to patient. The diameter of a healthy infra-renal aorta (101) close to the bifurcation can be between about 10 mm to about 20 mm. In some embodiments, the diameter of a healthy infra-renal aorta close to the bifurcation can be 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, between about 5 mm and about 15 mm, or between about 15 mm and about 25 mm. The diameters of the right and left common iliac arteries (103a-b) can be different. The diameters of common iliac arteries (103a-b) can vary from between about from 7 mm to about 14 mm. In other embodiments, the diameters of the common iliac arteries can be 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, between about 5 mm and about 10 mm, or between about 10 mm and about 20 mm.

The length of the left and right common iliac artery (103a-b) can be different. The length of the left and right common iliac artery (103a-b) can be between about 20 mm and about 80 mm. In some embodiments, the length of the left and right common iliac artery can be between about 20 mm and about 30 mm, between about 30 mm and about 40 mm, between about 40 mm and about 50 mm, between about 60 mm and about 70 mm, or between about 70 mm and about 80 mm. Aorto-iliac occlusive disease can reduce the diameters of infra-renal aorta (101) and common iliac arteries (103a-b). This is depicted by plaque (106).

Figure 2:
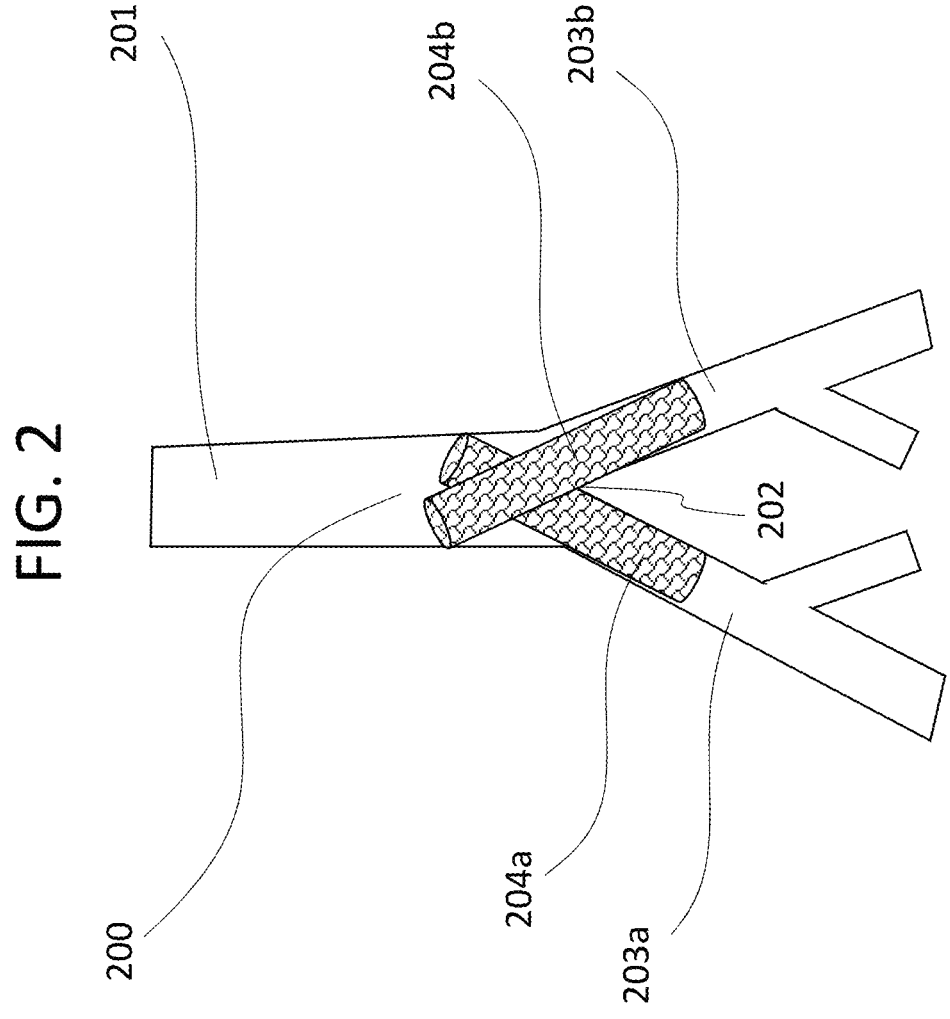
FIG. 2 illustrates the kissing stent technique to treat an aorto-iliac bifurcation.

FIG. 2 illustrates two kissing stents (204a-b) placed into aorto-iliac arteries (200) to treat AIOD. Stents (204a-b) extend from common iliac arteries (203a-b) across aorto-iliac bifurcation (202) into aorta (201). Stents (204a-b) can be bare metal stents or covered stents. Stents (204a-b) can be balloon-expanded or self-expandable. Stents (204a-b) typically cross over at aorto-iliac bifurcation (202). Since the distal ends of stents (204a-b) do not conform to the wall of aorta (201), flow disturbances can be created at the distal end of stents (204a-b). Also, stents (204a-b) make it difficult to advance a guidewire or catheter from one iliac artery (203a-b) over bifurcation (202) to the other iliac artery (203a-b).

Figure 3:
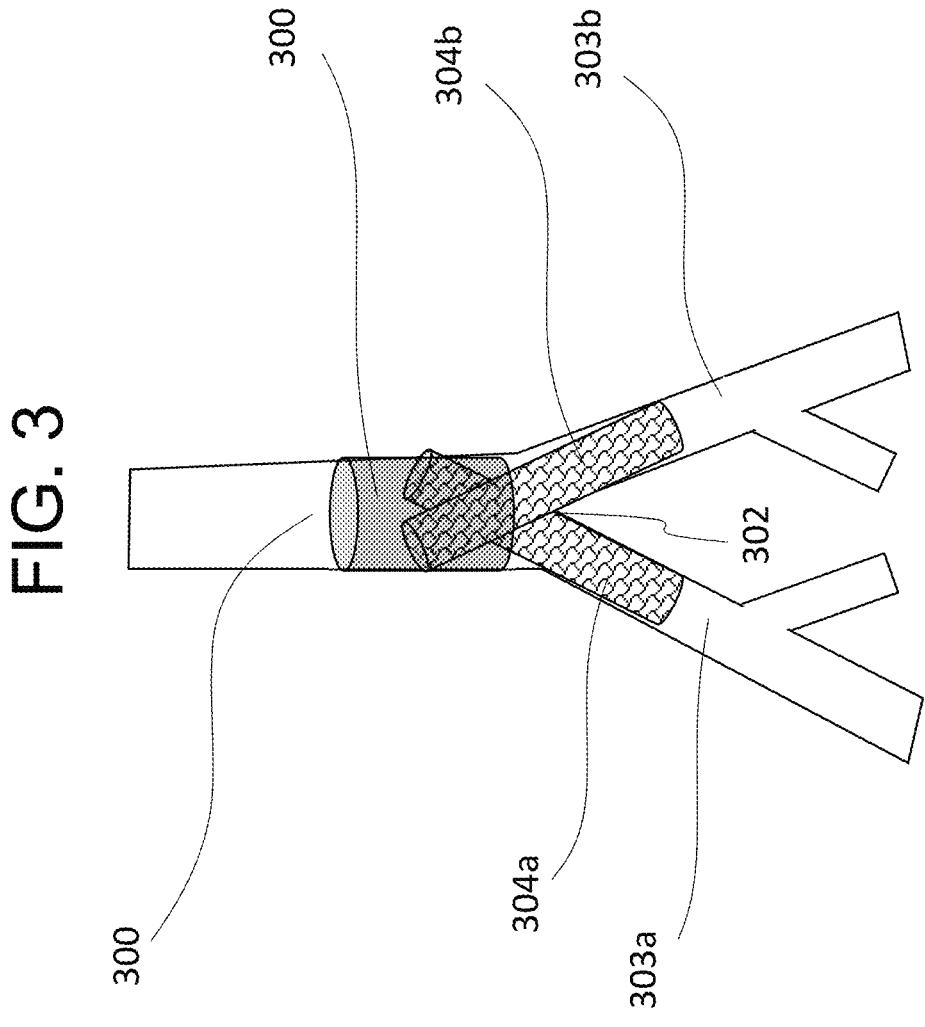
FIG. 3 illustrates the CERAB technique to treat an aorto-iliac bifurcation.

FIG. 3 shows the CERAB technique for treating AIOD. First covered stent (300) is placed in aorta (301) close to aorto-iliac bifurcation (302). Subsequently, a pair of covered stents (304a-b) are placed across aorto-iliac bifurcation (302) using the kissing stent technique. The distal ends of stents (304a-b) are placed inside the lumen of first covered stent (300). The proximal ends of stents (304a-b) are placed into iliac arteries (303a-b). Since the distal ends of stents (304a-b) do not conform to the lumen of first covered stent (300), flow disturbances can be created at the distal end of stents (304a-b). Stents (304a-b) make it difficult to advance a guidewire or catheter from one iliac artery (303a-b) over aorto-iliac bifurcation (302) to the other iliac artery (303a-b).

In some embodiments, a system for treating a diseased bifurcating blood vessel comprises a bifurcated stent comprising a main body stent, a first branch stent, and a second branch stent; and a catheter for delivering the bifurcated stent into the diseased bifurcated blood vessel. The catheter can comprise a first balloon and a second balloon arranged substantially in parallel. In some embodiments, the first branch stent can be crimped onto the first balloon, the second branch stent can be crimped onto the second balloon, and the main body stent can be crimped onto the first balloon and the second balloon.

In other embodiments, the first balloon and the second balloon can comprise a waist positioned between the branch stents and the main body stent. In some embodiments, the catheter can further comprise an inflation port that is in fluid communications with the first balloon and second balloon. In other embodiments, the first and the second branch stents can be crimped into an oval cross-section. In some embodiments, the main body stent can be crimped into a circular cross-section.

In some embodiments, the catheter can further comprise a looped guidewire lumen that passes a guidewire through the first balloon and second balloon. The stent can be covered with a layer of biocompatible material.

In other embodiments, a method for treating a diseased bifurcating blood vessel including a main vessel and two branch vessels comprises: mounting a bifurcated stent including a main body stent and a first branch stent and a second branch stent onto a catheter having a first balloon and a second balloon; placing the bifurcated stent into the bifurcating blood vessel; expanding the first branch stent into the first branch vessel by inflating the first balloon; expanding the second branch stent into the second branch vessel by inflating the second balloon; and expanding the main body stent into the main vessel by simultaneously inflating the first balloon and the second balloon.

In some embodiments, the branch stents can be expanded from an oval cross-section into a circular cross-section. In other embodiments, the main body stent can be expanded from a circular cross-section into an oval cross-section.

In some embodiments, a balloon catheter for delivering a bifurcated stent into a bifurcated blood vessel comprises a proximal hub; a shaft; a first balloon connected to the shaft; a second balloon in fluid communication with the first balloon; an inflation port at the proximal hub in fluid communication with the first balloon and second balloon; a first guidewire lumen extending through the proximal hub, the shaft, and the first balloon; and a second guidewire lumen extending through the proximal hub, the first balloon, and the second balloon.

In other embodiments, the two balloons can be cylindrical in shape and have a narrowing in the midsection. The two balloons can be arranged in a substantially parallel configuration when inserted into the bifurcated blood vessel. The two balloons can be arranged in an expandable configuration when inflated in the bifurcated blood vessel. The two balloons can be arranged in series when removed from the bifurcated blood vessel.

Figure 4:
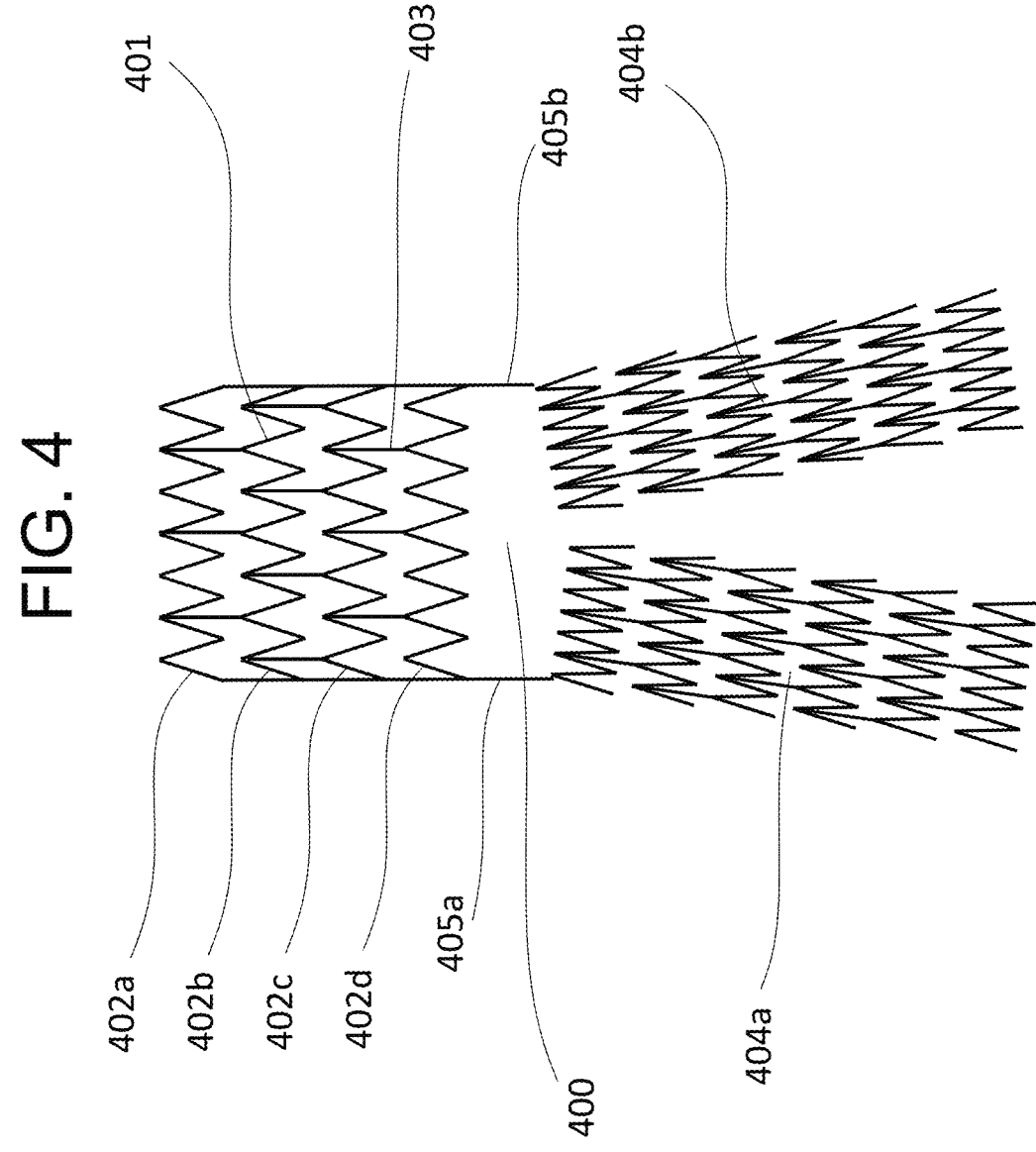
FIG. 4 illustrates a bifurcated stent described herein.

A bifurcated stent as described herein is illustrated by FIG. 4. FIG. 4 depicts bifurcated stent (400). The main body stent (401) can comprise stent rings of any shape. In some embodiments, stent rings (402a-d) are of zig-zag shape as illustrated in FIG. 4. Stent rings (402a-d) can be connected by generally axially oriented struts (403). Branch stents (404a-b) can be of similar design as main body stent (401). The three stents can be laser cut from a metal tube. The metal can be stainless steel, cobalt-chromium, any other metal alloy with low memory properties, or a combination thereof. Main body stent (401) can be connected to branch stents (404a-b) by welding the distal ends of branch stents (404a-b) to proximal struts (405a-b) of main body stent (401).

Figure 5A:
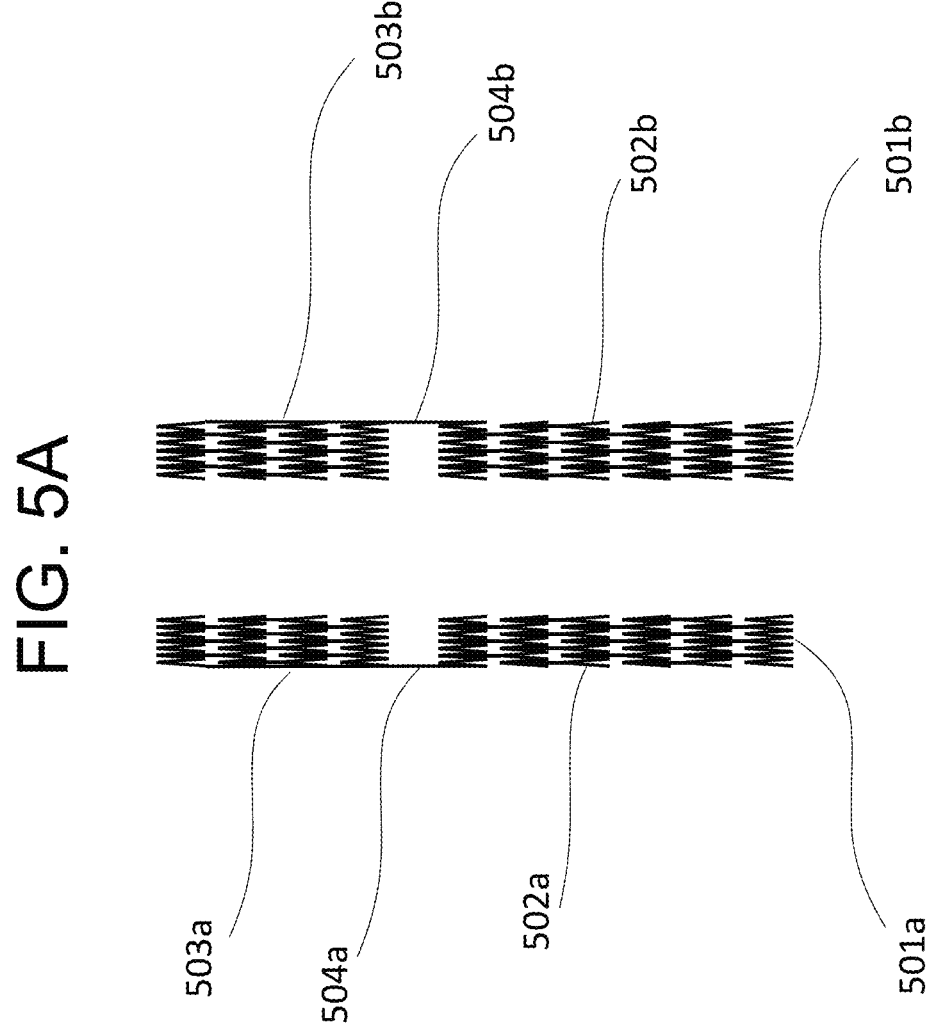
FIG. 5A illustrates two identical stents.
Figure 5B:
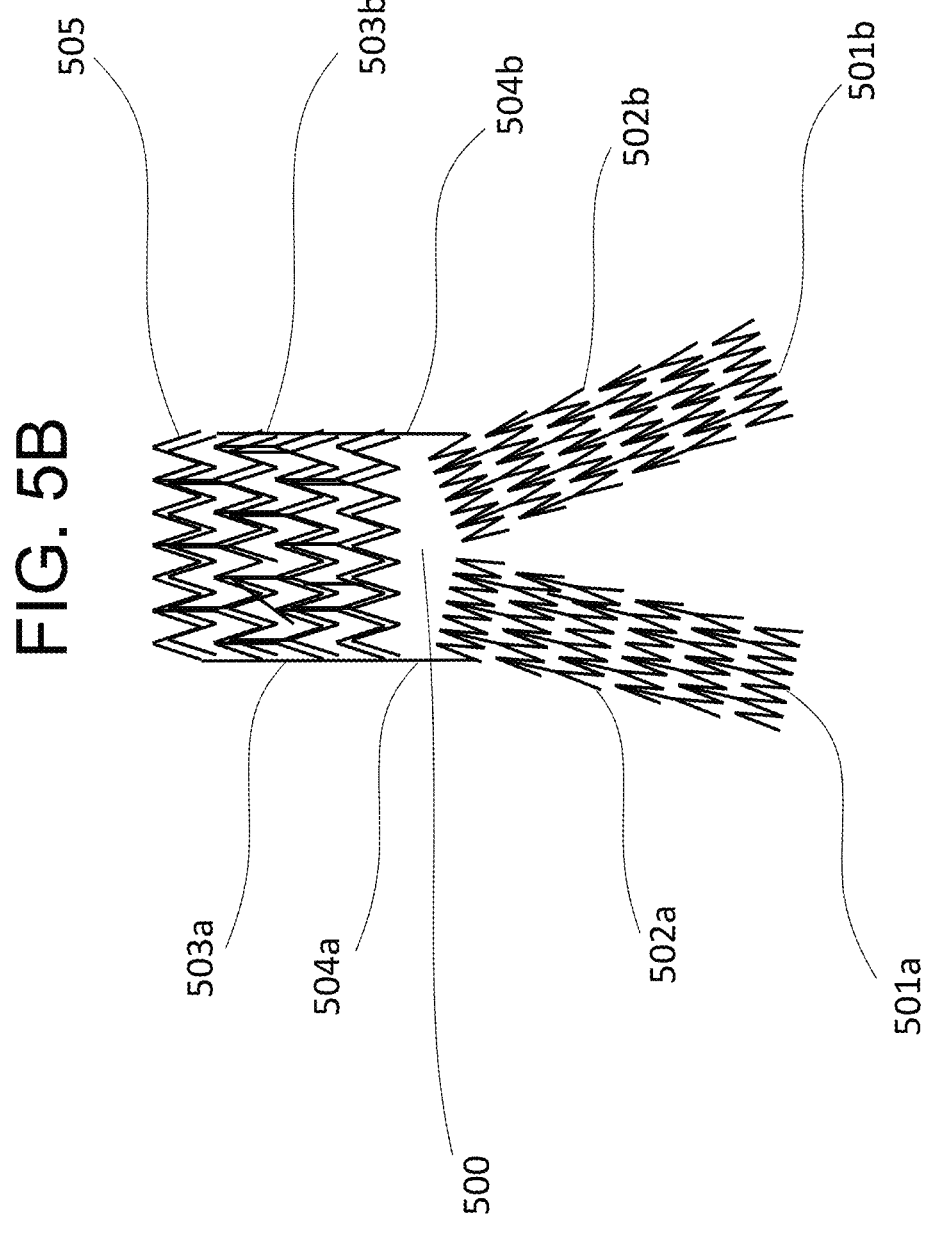
FIG. 5B illustrates a bifurcated stent that comprises the two identical stents of FIG. 5A.

FIGS. 5A-B show another embodiment of a bifurcated stent as described herein. FIG. 5 depicts bifurcated stent (500). In some embodiments, two identical stents (501 a-b) are used to form bifurcated stent (500) as illustrated in FIGS. 5A-B. The proximal sections of stents (502a-b) are designed to form the respective iliac sections of bifurcated stent (501), and the distal sections of stents (503a-b) are designed to overlap and form main body (505) of bifurcated stent (500) as shown in FIG. 5B. Struts (504a-b) can connect the distal and proximal sections of stents (501a-b) and provide a section along stents (501 a-b) free of stent rings to avoid stent rings from obstructing the aortic bifurcation.

The diameter of the main body of the bifurcated stent can be between about 10 mm to about 30 mm. In some embodiments, the diameter of the main body of the bifurcated stent can be 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, between about 5 mm and about 15 mm, or between about 15 mm and about 30 mm. The diameters of the branch stents can be between about 5 mm to about 20 mm. In some embodiments, the diameters of the branch stents of the bifurcated stent can be 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, between about 4 mm and about 10 mm, or between about 9 mm and about 21 mm.

In other embodiments, the diameter of the main body of the bifurcated stent can be between about 10 mm to about 20 mm and the diameters of the branch stents can be about 5 mm to about 10 mm. The length of the main body stent can be between about 20 mm to about 100 mm and the lengths of the branch stents can be between about 20 mm to about 120 mm. In other embodiments, the length of the main body stent can be between about 30 mm to about 60 mm and the lengths of the branch stents can be between about 20 mm to about 50 mm. The left and right branch stents can be of the same diameter or of a different diameter. The left and right branch stents can of the same length or of a different length. The dimensions of the main body stent and the branch stents can be different than the ranges above, if the bifurcated stent is placed in a bifurcation in the body other than the aorto-iliac bifurcation.

Figure 6:
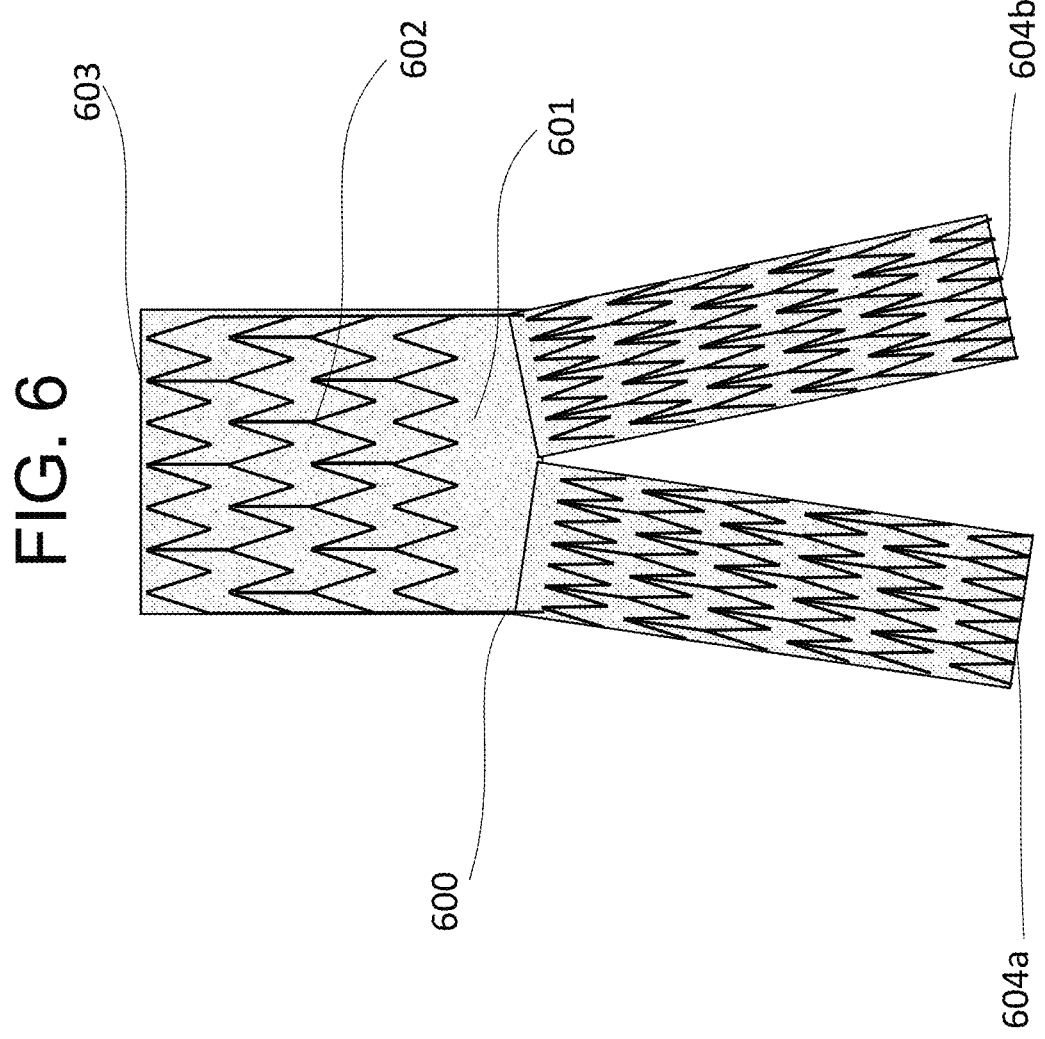
FIG. 6 illustrates a covered bifurcated stent described herein.

The bifurcated stent can be covered with a layer of polymer or animal tissue. FIG. 6 shows an embodiment of a covered bifurcated stent as described herein. Covered bifurcated stent (600) is depicted by FIG. 6. Cover (601) can be made from woven or knitted fibers, polymer(s), porous material, or non-porous material. Cover (601) material can be made from polyurethane, PET (polyethylene terephthalate), non-expanded PTFE (polytetrafluoroethylene) or expanded ePTFE. Cover (601) can be connected to stent (602) on the distal end of main body (603) and the proximal ends of branch stents (604a-b). In some embodiments, cover (601) can be connected to a portion of bifurcated stent (602). In other embodiments, cover (601) can be connected to the entire bifurcated stent (602). Cover (601) can be connected to bifurcated stent (602) by fibers or sutures. Cover (601) can be connected to bifurcated stent (602) by adhesives. Cover (601) can be external to bifurcated stent (602). Cover (601) can be internal to bifurcated stent (602). Bifurcated stent (602) can be sandwiched between two layers of cover (601). The two layers of cover (601) can be bonded or fused together. The cover can be sandwiched between two layers of bifurcated stent (602).

Figure 7:
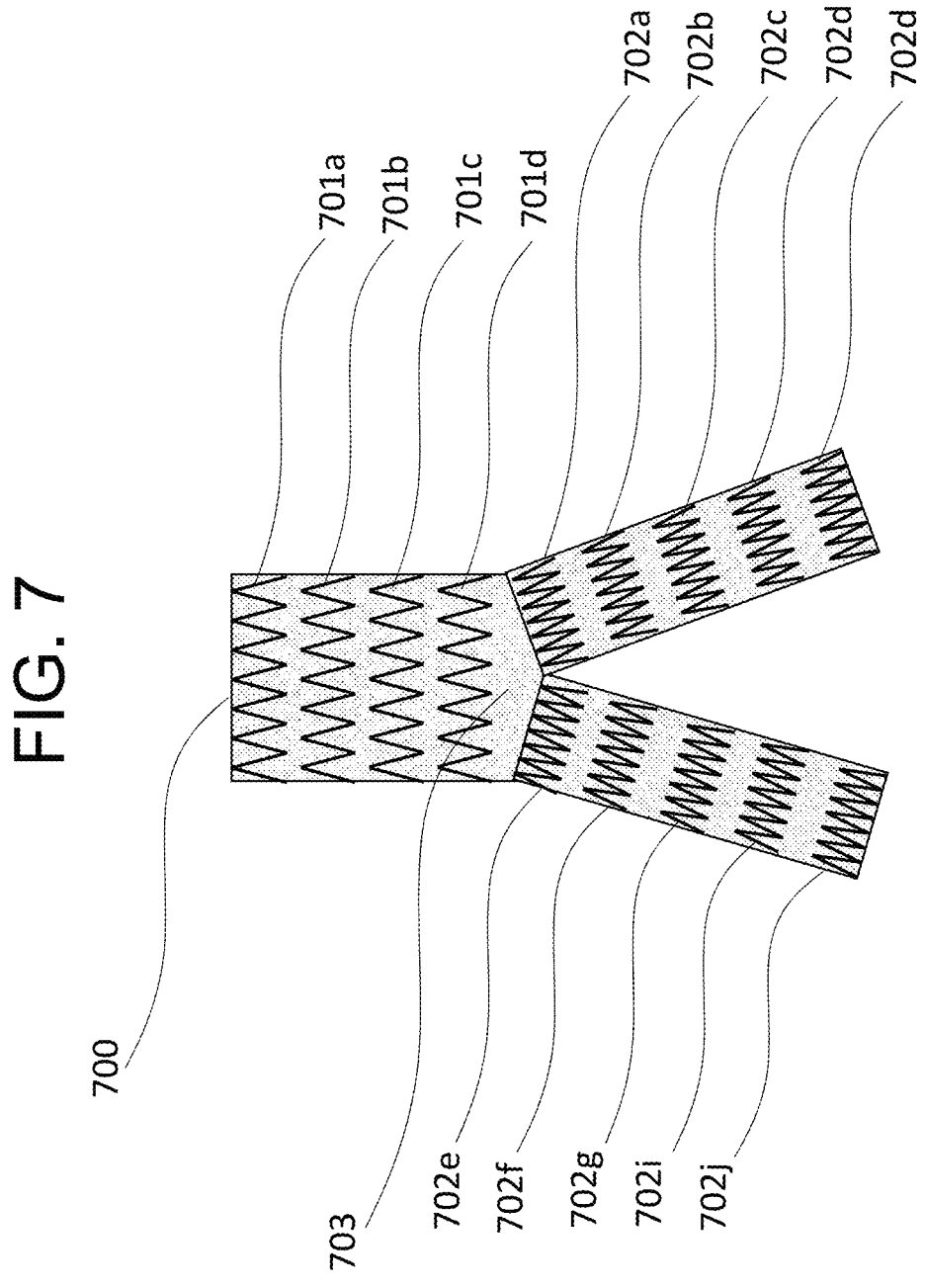
FIG. 7 illustrates another covered bifurcated stent described herein.

FIG. 7 shows another embodiment of a covered bifurcated stent described herein. Covered bifurcated stent (700) is depicted by FIG. 7. Individual main body stent rings (701a-d) and branch stent rings (702a-j) are not connected by metal struts. Polymeric bifurcated cover (703) is bonded to main body stent rings (701 a-d) and branch stent rings (702a-j). The individual stent rings can be formed from a metal wire or can be cut from a metal tube. Some of the stent rings can be connected by struts similar to the embodiment of the bifurcated stent illustrated in FIG. 4.

Figure 8:
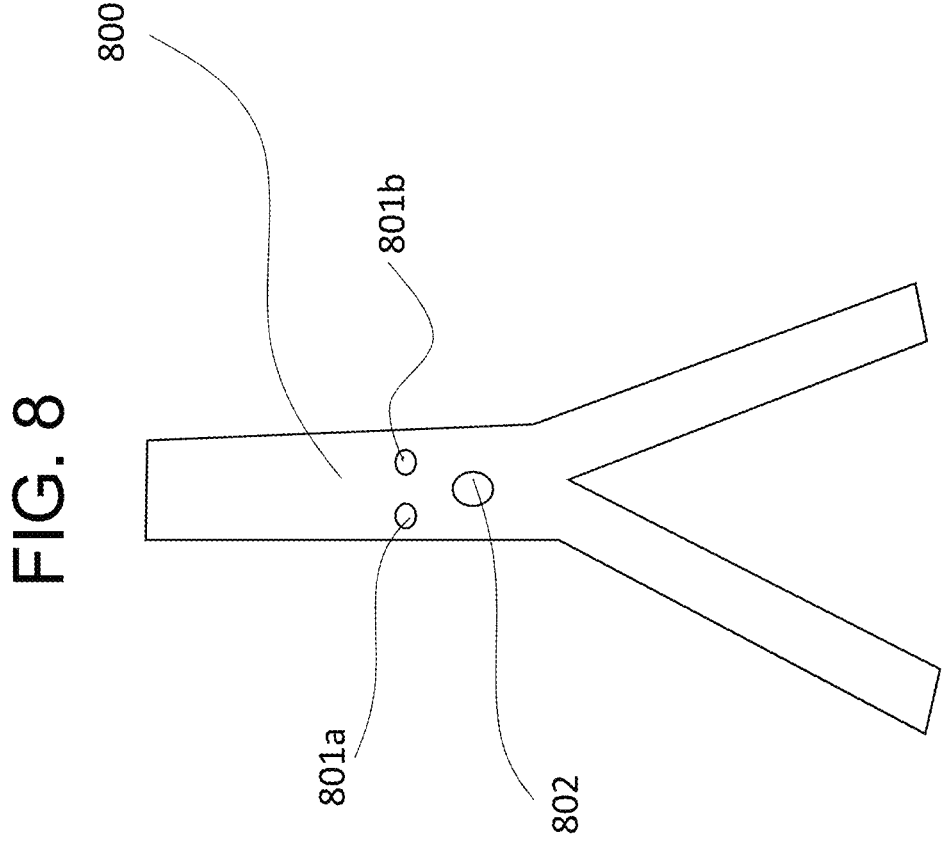
FIG. 8 illustrates an aorto-iliac bifurcation with branch vessels in the infra-renal aorta.

FIG. 8 shows further details of the infra-renal aorta. Several arteries branch from intrarenal aorta (800) including pairs of lumber arteries (801 a-b) and inferior mesenteric artery (802). Placement of a covered bifurcated stent into the aorto-iliac bifurcation can obstruct the blood flow into these arteries and cause ischemia of the organs perfused by these arteries.

Figure 9:
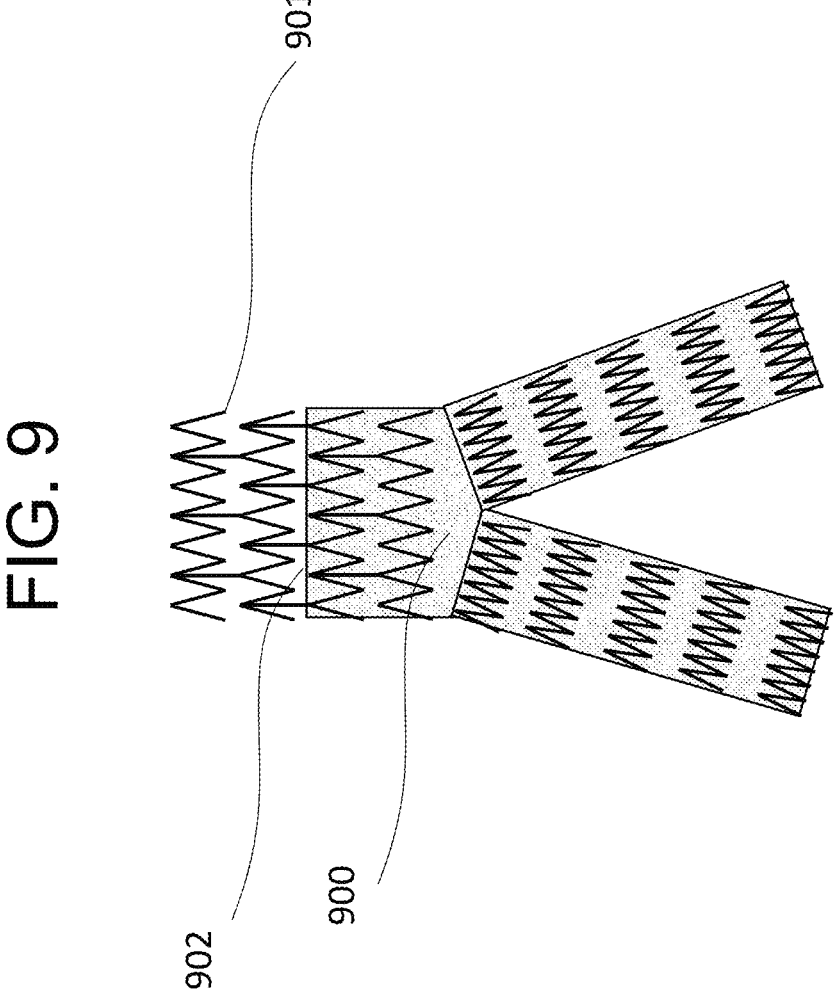
FIG. 9 illustrates an embodiment of a partially covered bifurcated stent described herein.

FIG. 9 shows an embodiment of a covered bifurcated stent (900) described herein to avoid obstruction of branch arteries in the infra-renal aorta. The distal segment of main body stent (901) is not covered. When placed into the aorto-iliac bifurcation, the distal end of cover (902) can be below the location of the inferior mesenteric artery.

Figure 10:
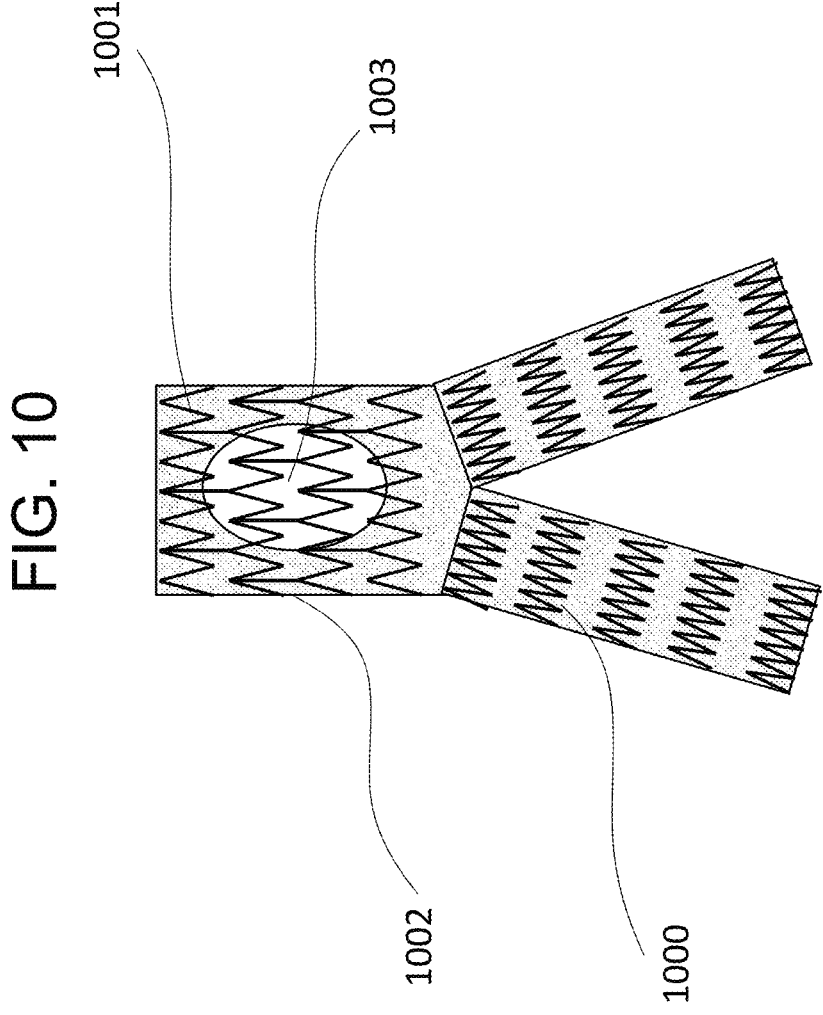
FIG. 10 illustrates another embodiment of a partially covered bifurcated stent described herein.

FIG. 10 shows another embodiment of a covered bifurcated stent (1000) described herein to avoid obstruction of branch arteries in the infra-renal aorta. When placed into the aorto-iliac bifurcation, an opening (1003) in cover (1002) of main body (1001) allows for blood flow into the branch arteries of the infra-renal aorta. Cover (1002) can have a single opening or multiple openings.

Figure 11:
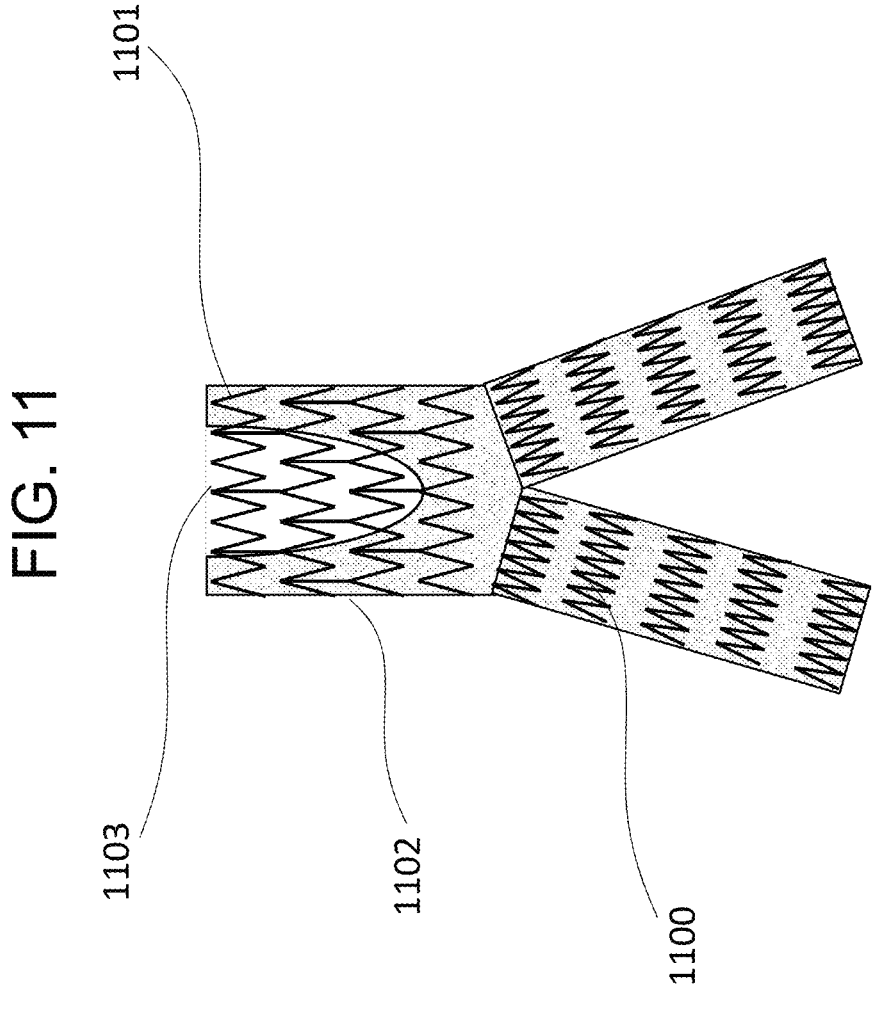
FIG. 11 illustrates another embodiment of a partially covered bifurcated stent described herein.

FIG. 11 shows another embodiment of a covered bifurcated stent (1100) described herein to avoid obstruction of branch arteries in the infra-renal aorta. Cover (1102) of main body stent (1101) has cut-out (1103) extending to the distal end of main body stent (1101). Cut-out (1103) allows for blood flow into branch arteries of the infra-renal aorta. Cover (1102) can include a single cut-out or multiple cut-outs.

Figure 12A:
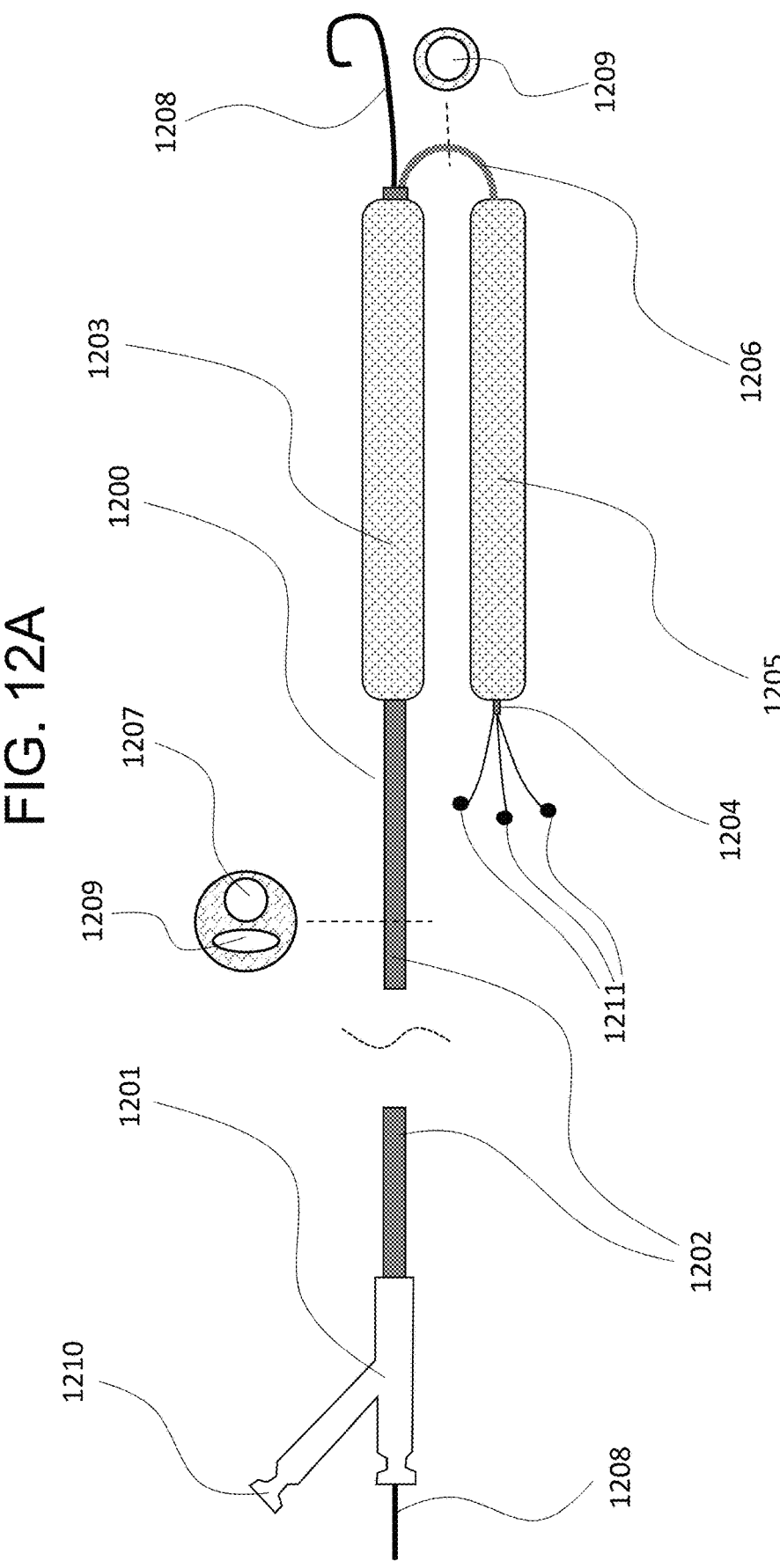
FIG. 12A illustrates an embodiment of a catheter for delivering a bifurcated stent with the catheter in a first configuration.
Figure 12B:
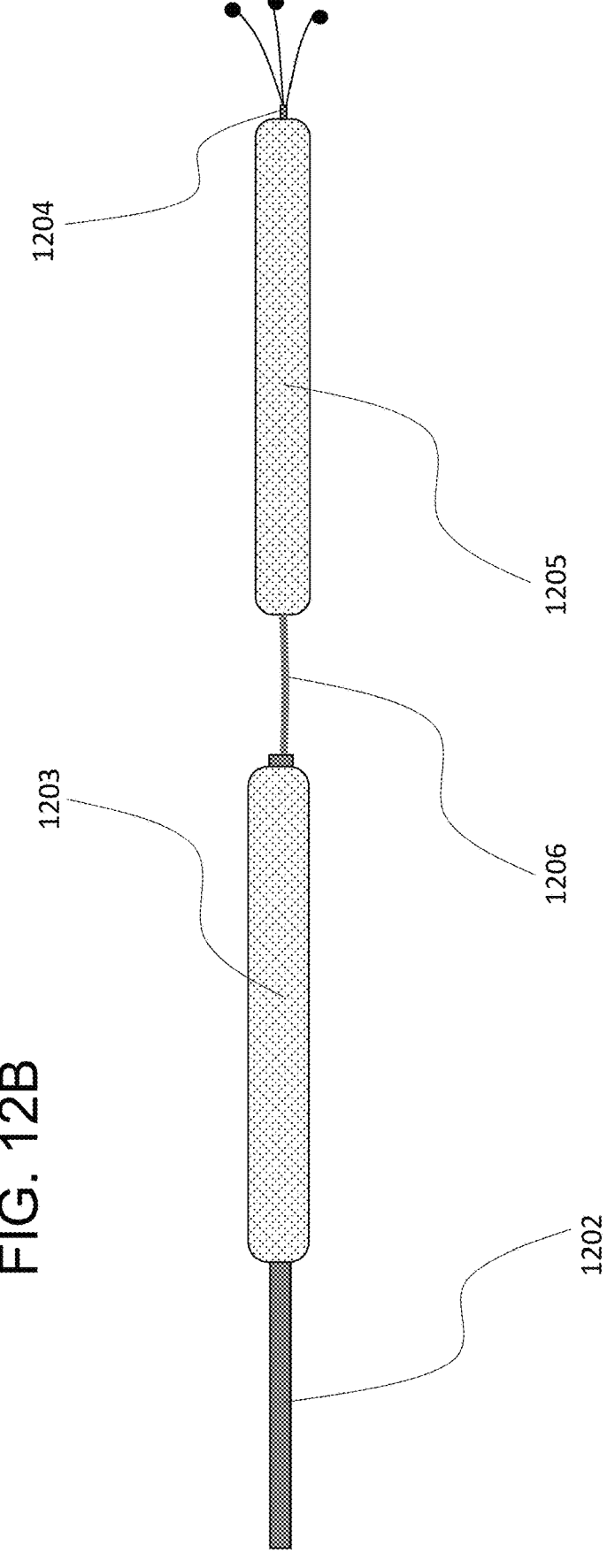
FIG. 12B illustrates the catheter of FIG. 12A in a second configuration or serial configuration.

FIGS. 12A-B illustrate an embodiment of a catheter as described herein for percutaneous delivery of a bifurcated stent into the aorto-iliac bifurcation. FIG. 12A illustrates a first configuration of catheter (1200). Catheter (1200) comprises proximal hub (1201), proximal shaft (1202), first balloon (1203) mounted onto proximal shaft (1202), distal shaft (1204), second balloon (1205) mounted onto distal shaft (1204), and shaft connector (1206) connecting proximal shaft (1202) to distal shaft (1204). The arrangement of proximal balloon (1203) and distal balloon (1205) shown in FIG. 12B is referred to as a serial configuration. The arrangement of proximal balloon (1203) and distal balloon (1205) shown in FIG. 12A is referred to as a parallel configuration. Catheter (1200) includes first guidewire lumen (1207) extending from proximal end of the hub (1201) to an opening at the distal end of proximal shaft (1202). Guidewire lumen (1207) is designed to accommodate guidewire (1208) which is placed from the ipsi-lateral access vessel into the aorta. Inflation lumen (1209) extends from inflation port (1210) to distal shaft (1204) and is in fluid communication with distal balloon (1205) and proximal balloon (1203). Shaft connector (1206) which houses inflation lumen (1209) can be flexible to allow shaft connector (1206) to be bent from a straight configuration (FIG. 12B) into a 180-degree curved configuration (FIG. 12A) without collapse or obstruction of inflation lumen (1209). Shaft connector (1206) can be made from a low-durometer polymer or memory alloy. Shaft connector (1206) can be reinforced by a metal coil. Snaring mechanism (1211) can be attached to the distal end of distal shaft (1204) to facilitate the capturing of the distal end of catheter (1200) with a snare. Snaring mechanism (1211) can include an antenna-like structure or an array of antenna-like structures. Snaring mechanism (1211) can be straight, coiled, or of any shape that facilitates the placement of the loop of the snare over the distal end of catheter (1200). Snaring mechanism (1211) can be radiopaque or can have radiopaque markers attached to the distal ends of snaring mechanism (1211).

Figure 13A:
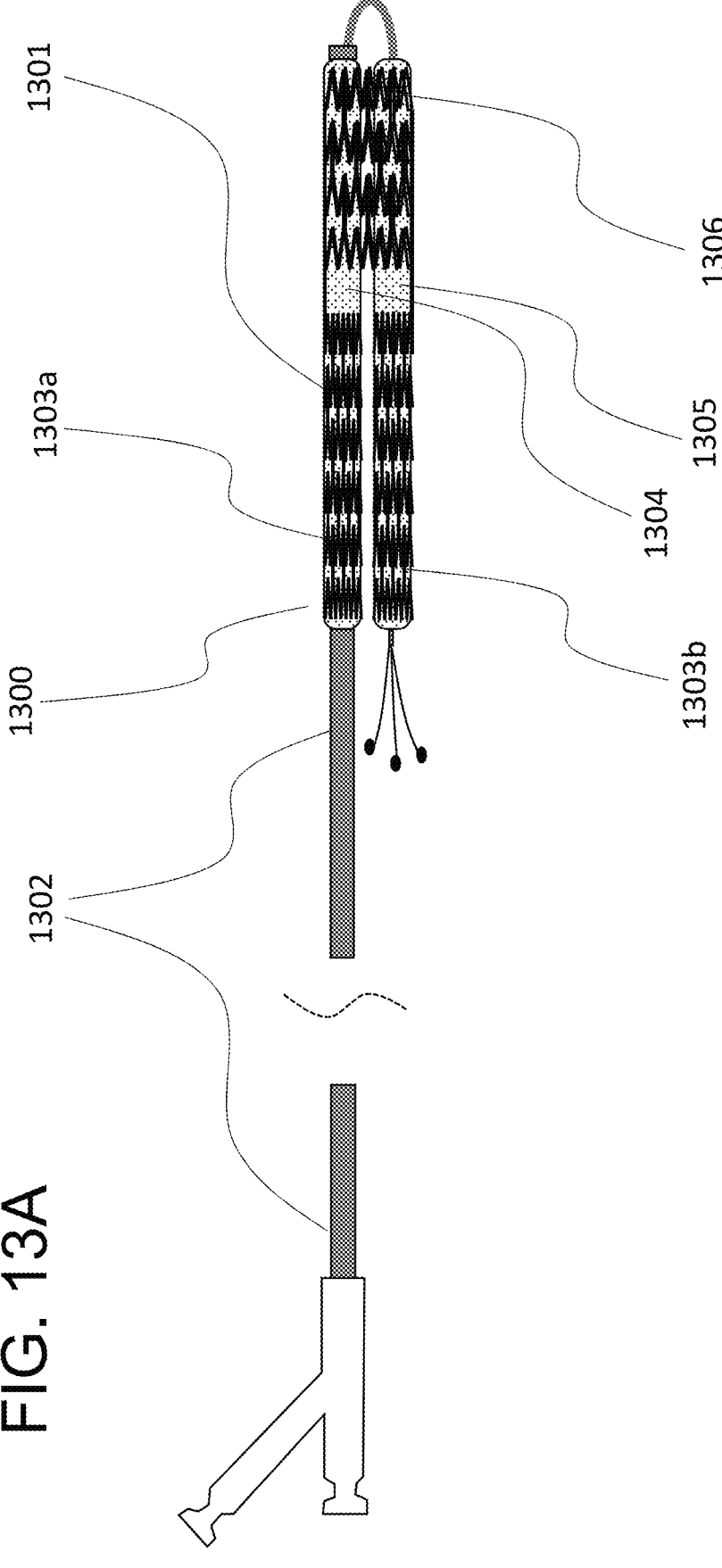
FIG. 13A illustrates a bifurcated stent system with balloons in a collapsed configuration and a bifurcated stent in a crimped configuration.
Figure 13B:
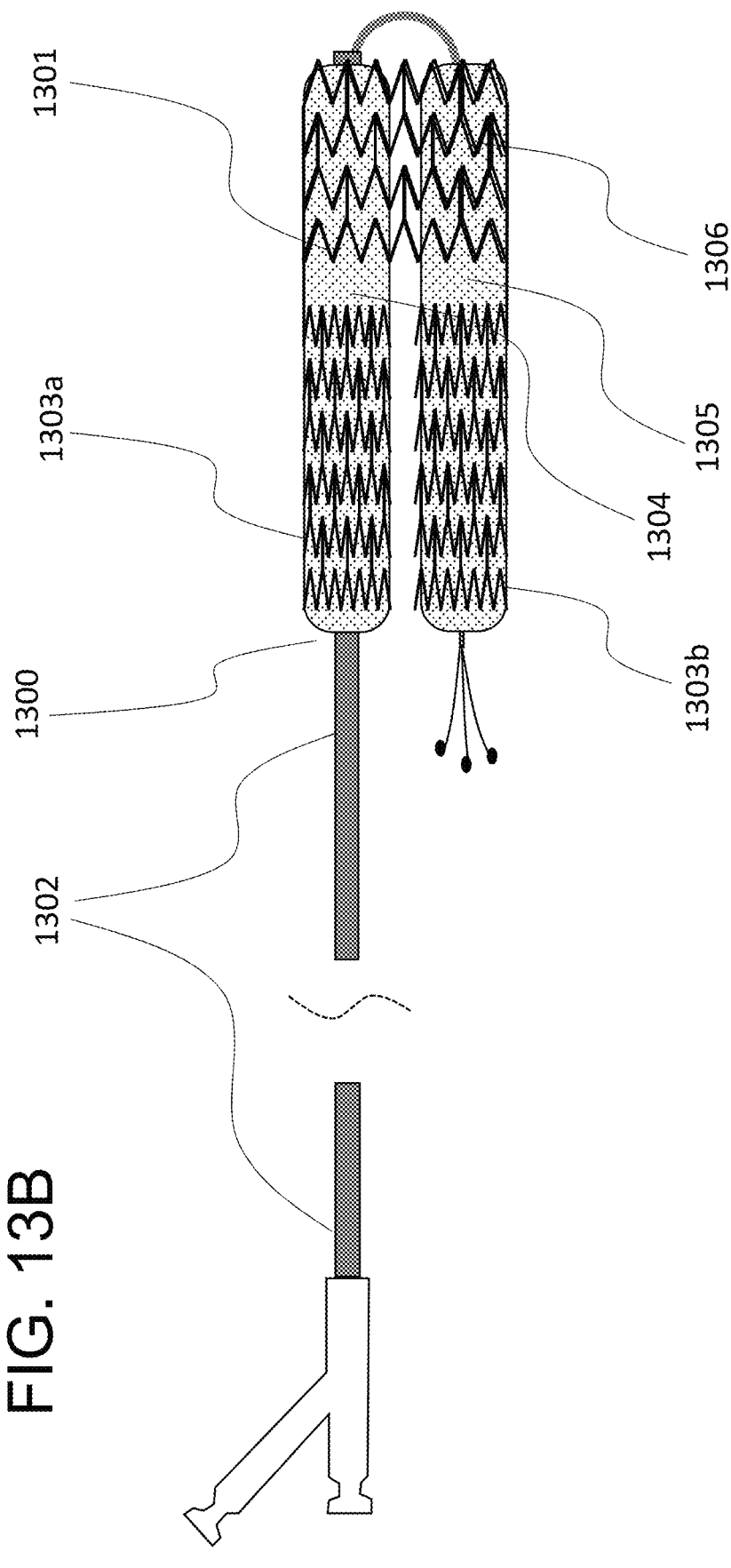
FIG. 13B illustrates the bifurcated stent system of FIG. 13A with the balloons in an inflated configuration and the bifurcated stent in an expanded configuration.

FIGS. 13A-B show an embodiment of the bifurcated stent system (1300) as described herein comprising bifurcated stent (1301) illustrated by FIGS. 5A-B and catheter (1302) illustrated by FIGS. 12A-B for percutaneous delivery of bifurcated stent (1301) to the aorto-iliac bifurcation. First balloon (1304) and second balloon (1305) are in a substantially parallel configuration. First branch stent (1303a) is mounted onto first balloon (1304) and second branch stent (1303b) is mounted onto second balloon (1305). Main body stent (1306) is mounted on both first balloon (1304) and second balloon (1305). FIG. 13A shows bifurcated stent system (1300) with the balloons (1304-1305) in the collapsed configuration and bifurcated stent (1301) in the crimped configuration. FIG. 13B shows bifurcated stent system (1300) with balloons (1304-1305) in the inflated configuration and bifurcated stent (1301) in the expanded configuration.

Figure 14:
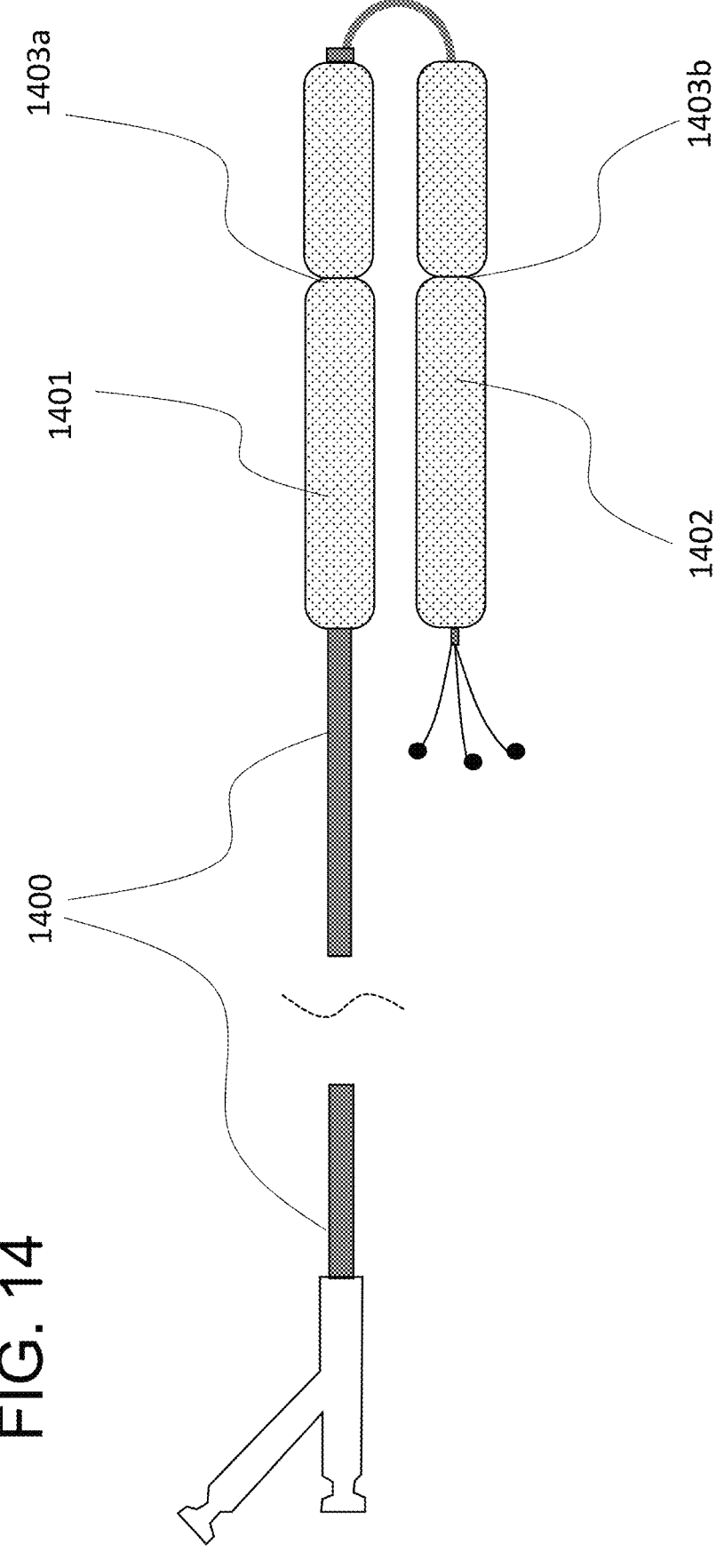
FIG. 14 illustrates another embodiment of a catheter for delivering a bifurcated stent.

FIG. 14 shows another embodiment of a catheter described herein. Catheter (1400) is illustrated in FIG. 14. First balloon (1401) and second balloon (1402) feature waists (1403a-b) where the diameter of balloons (1401-1402) is reduced. The purpose of waists (1403a-b) is to increase the bending flexibility of balloons (1401-1402) when inflated.

Figure 15A:
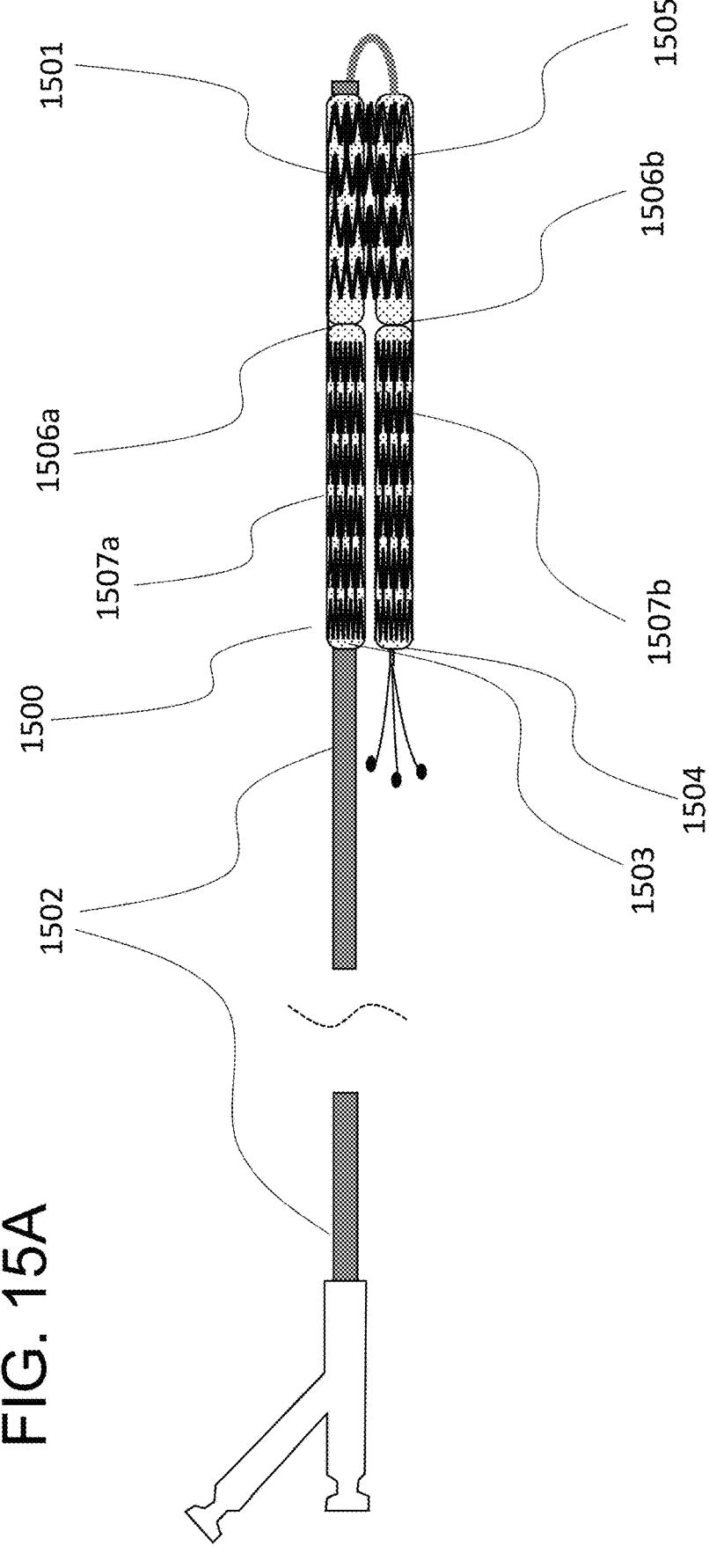
FIG. 15A illustrates a bifurcated stent system with balloons in a collapsed configuration and a bifurcated stent in a crimped configuration.
Figure 15B:
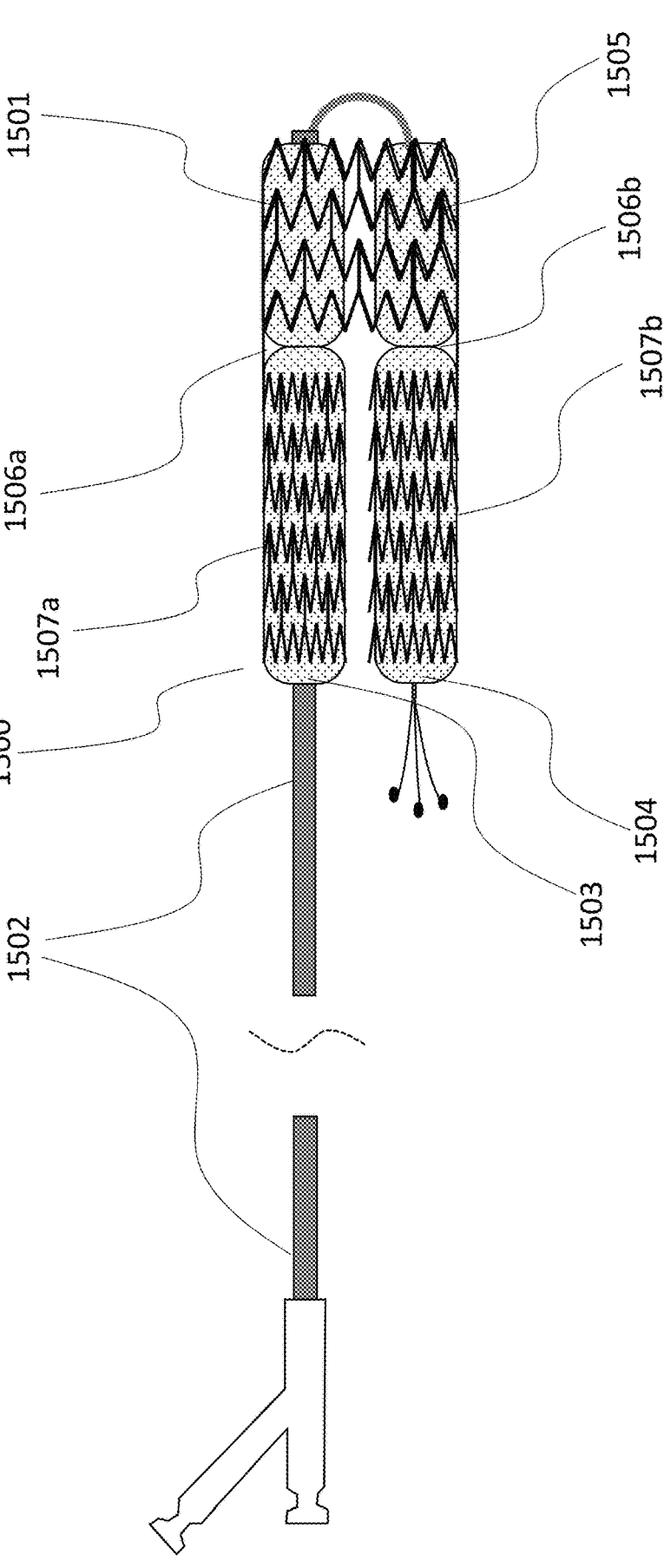
FIG. 15B illustrates a bifurcated stent system of FIG. 14A with the balloons in an inflated configuration and the bifurcated stent in an expanded configuration.

FIGS. 15A-15B show another embodiment of the bifurcated stent system (1500) described herein comprising a bifurcated stent (1501), and catheter (1502) as illustrated by FIG. 14. The locations of waists (1506a-b) in balloons (1503-1504) are aligned with the gaps between branch stents (1507a-b) and main body stent (1505). FIG. 15A shows bifurcated stent system (1500) with balloons (1503-1504) in the collapsed configuration and bifurcated stent (1501) in the crimped configuration. FIG. 15B shows bifurcated stent system (1500) with balloons (1503-1504) in the inflated configuration and bifurcated stent (1501) in the expanded configuration.

Figure 16:
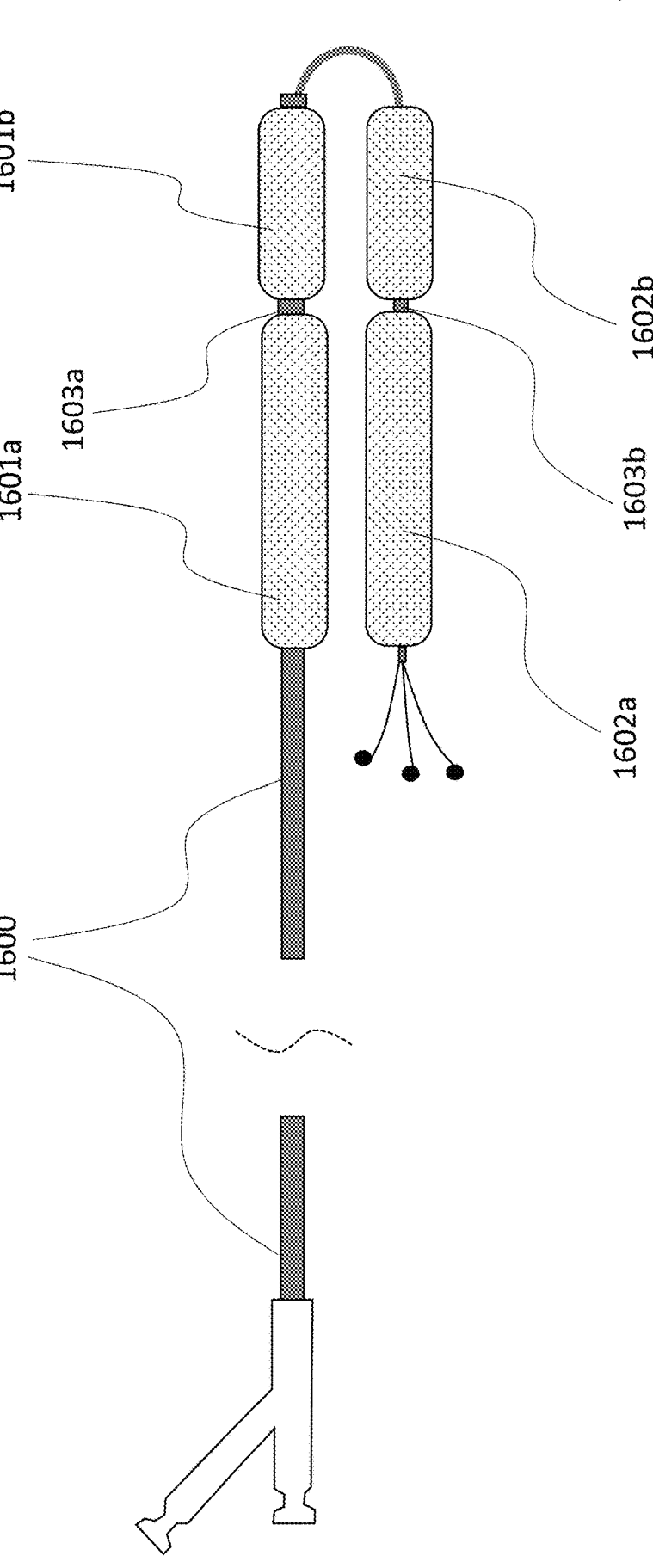
FIG. 16 illustrates another embodiment of a catheter for delivering a bifurcated stent.

FIG. 16 shows another embodiment of a catheter as described herein. Catheter (1600) is depicted in FIG. 16. The first pair of balloons (1601a-b) and the second pair of balloons (1602a-b) are arranged in parallel. The location of shaft sections (1603a-b) are aligned with the gaps between the branch stents and the main body stents (not shown) similar to waists (1503a-b) shown in FIGS. 15A-B. In some embodiments, the diameters and shapes of first pair of balloons (1601a, 1602a) can be different from the diameters or shapes of second pair of balloons (1601 b, 1602b). In some embodiments, the diameters and shapes of first pair of balloons (1601a, 1602a) and second pair of balloons (1601b, 1602b) can be the same. In other embodiments, the diameters of first pair of balloons (1601a, 1602a) can be close to the diameters of the iliac arteries. In some embodiments, the diameters of second pair of balloons (1601b, 1602b) can be close to one half of the diameter of the aorta.

Figure 17:
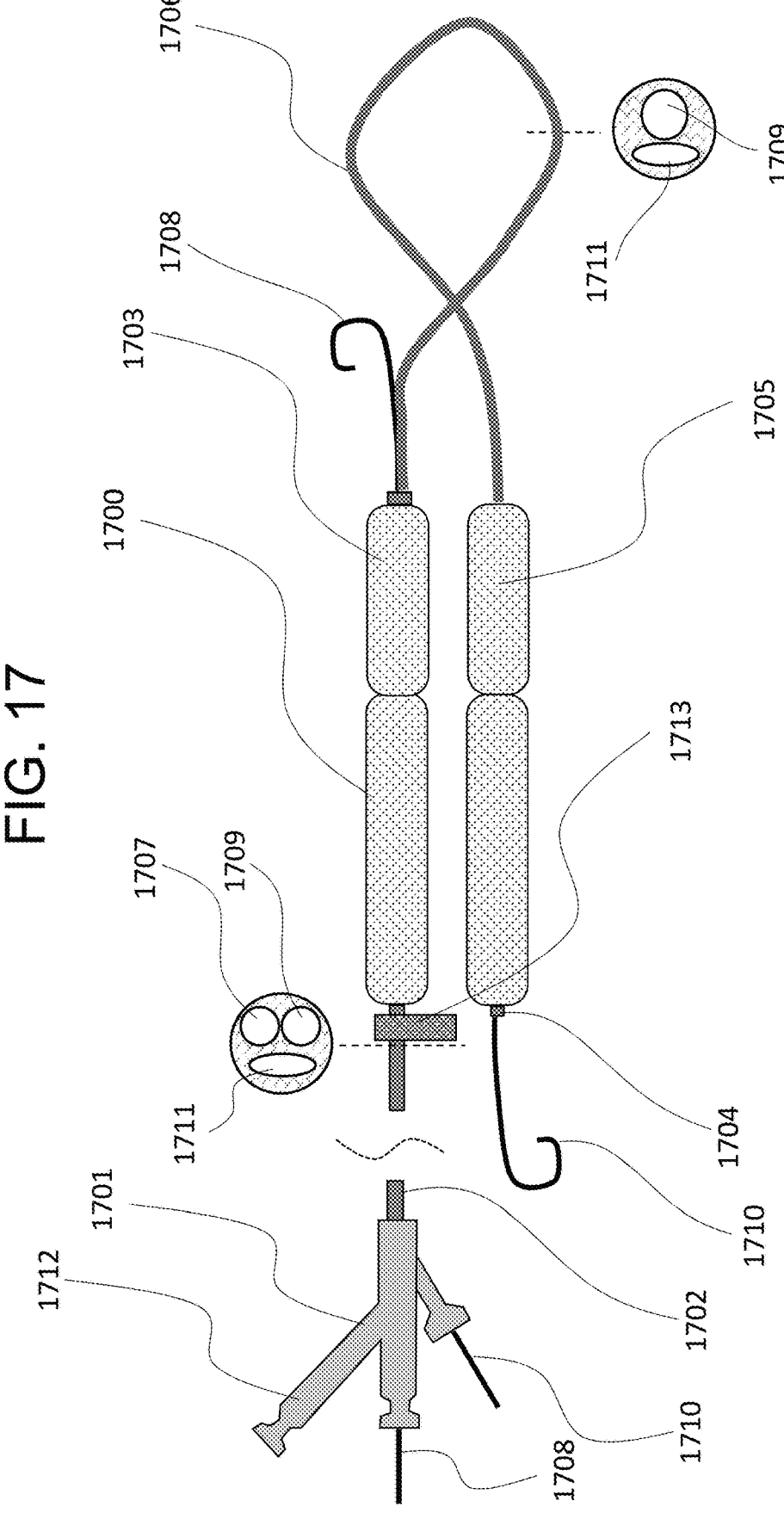
FIG. 17 illustrates another embodiment of a catheter for delivering a bifurcated stent.

FIG. 17 shows another embodiment of a catheter described herein for percutaneous delivery of a bifurcated stent into the aorto-iliac bifurcation. Catheter (1700) comprises proximal hub (1701), proximal shaft (1702), first balloon (1703) mounted onto proximal shaft (1702), distal shaft (1704), second balloon (1705) mounted onto distal shaft (1704), and shaft connector (1706) connecting proximal shaft (1702) to distal shaft (1704). Catheter (1700) includes first guidewire lumen (1707) extending from the proximal end of hub (1701) to an opening at the distal end of proximal shaft (1702). First guidewire lumen (1707) is designed to accommodate first guidewire (1708) which is placed from the ipsi-lateral access vessel into the aorta. Catheter (1700) includes second guidewire lumen (1709) extending from an opening in hub (1701) to an opening at the distal end of distal shaft (1704). Second guidewire lumen (1709) is designed to accommodate second guidewire (1710) which is placed from the ipsi-lateral access vessel to the contra-lateral iliac artery. Inflation lumen (1711) extends from inflation port (1712) to distal shaft (1704) and is in fluid communication with first balloon (1703) and second balloon (1705).

Shaft connector (1706) houses inflation lumen (1711) and second guidewire lumen (1709). Shaft connector (1706) forms a loop when first balloon (1703) and second balloon (1705) are in a substantially parallel configuration. The radius of curvature of the loop of shaft connector (1706) can be substantially larger than the radius of curvature of shaft connector (1206) in FIGS. 12A-B. The larger curvature facilitates the passage of second guidewire (1710) through shaft connector (1706). Shaft connector (1706) can be made from a low-durometer polymer or memory alloy. Shaft connector (1706) can be reinforced by a metal coil. Proximal shaft (1702) can include alignment feature (1713). Alignment feature (1713) is in axial contact with the distal end of distal shaft (1704) when the bifurcated stent is crimped onto catheter (1700). Alignment feature (1713) aligns first balloon (1703) and second balloon (1705) in the parallel configuration.

Figure 18A:
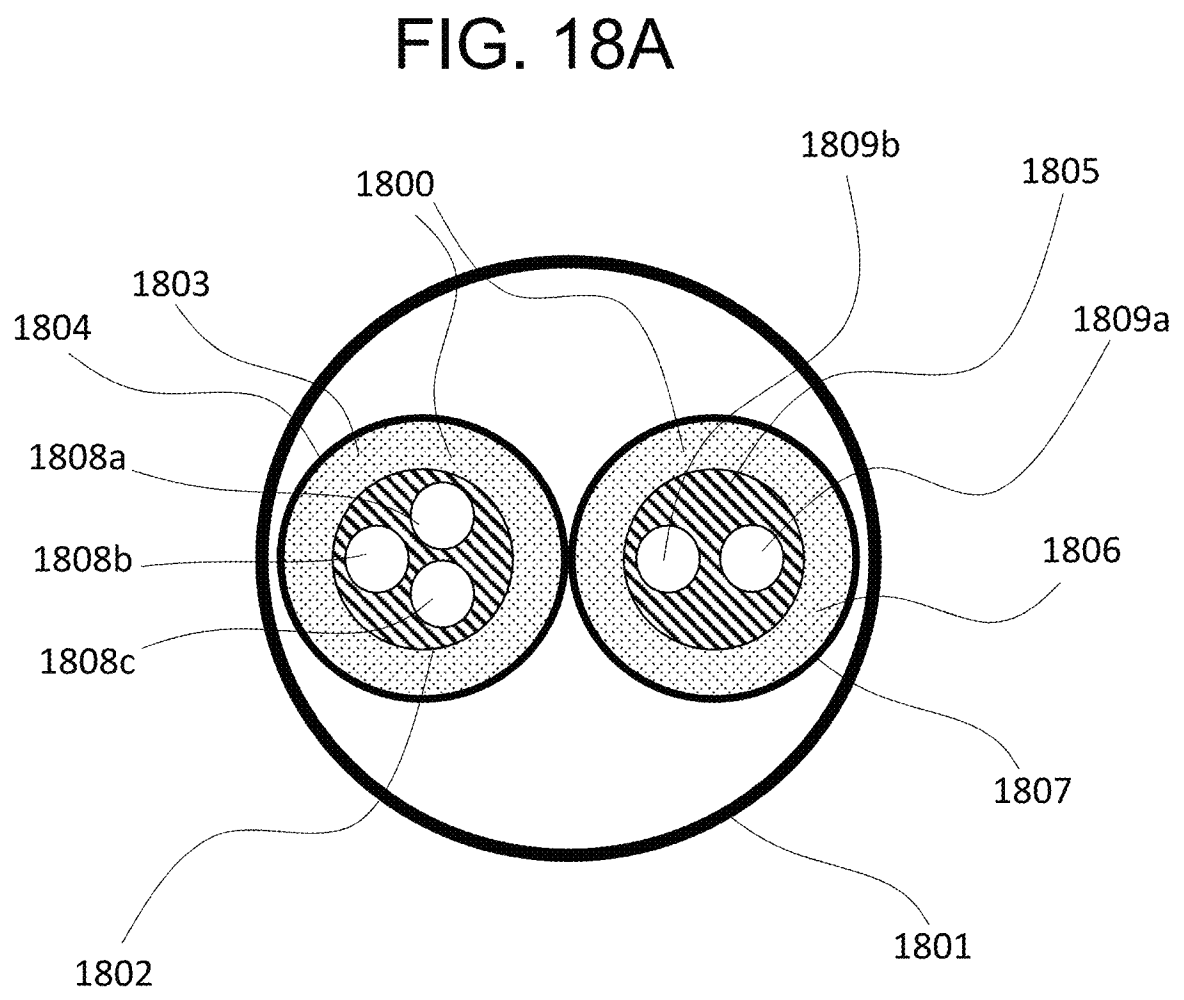
Figure 18B:
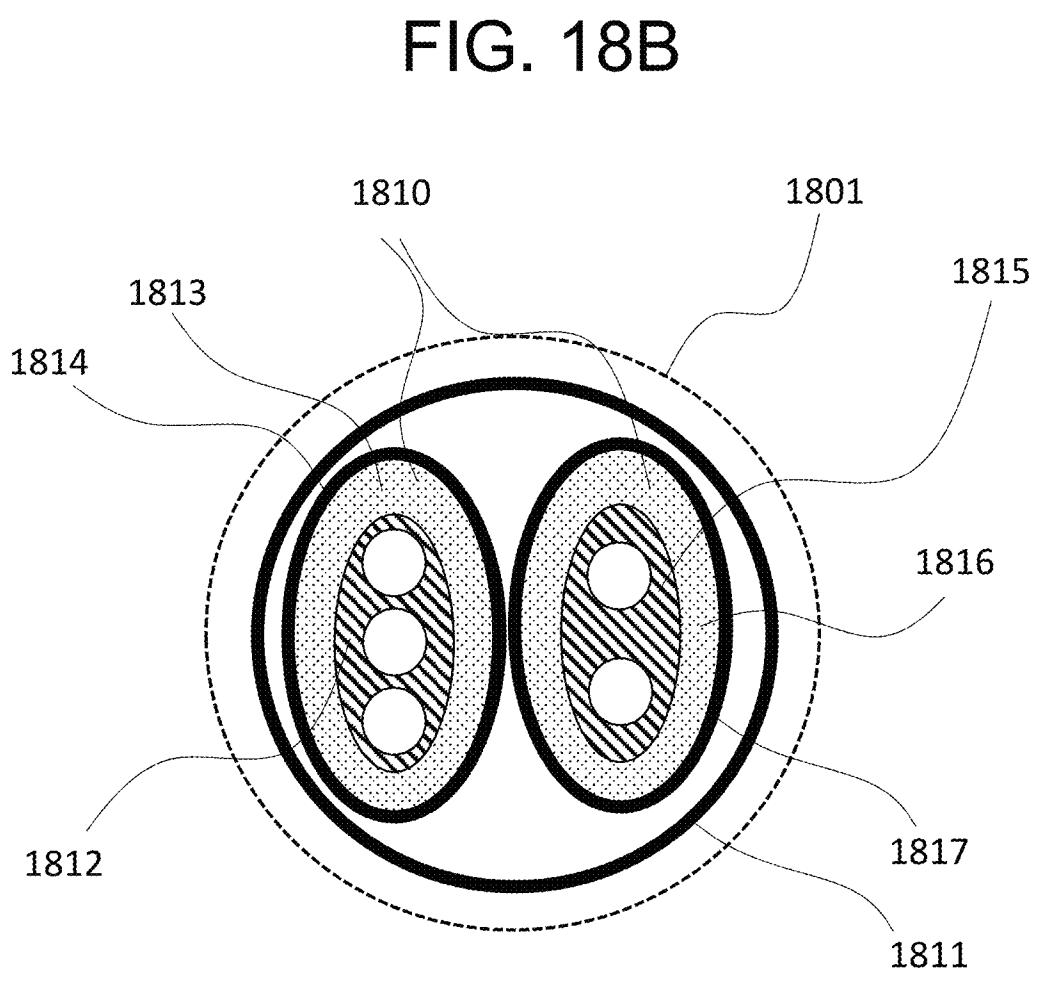

FIGS. 18A-18B show cross-sectional views of catheter (1800) in the parallel configuration placed into introducer sheath (1801). FIG. 18A shows a cross-sectional view of an embodiment of catheter (1800) as described herein in the parallel configuration placed into introducer sheath (1801). The cross sections of proximal shaft (1802), first balloon (1803), and first branch stent (1804) are co-axially aligned and distal shaft (1805), second balloon (1806), second branch stent (1807) are co-axially aligned. Proximal shaft (1802) includes three lumens (1808a-c); two guidewire lumens and one inflation lumen. Distal shaft (1805) includes two lumens (1809a-b); one guidewire lumen and one inflation lumen. In some embodiments, for catheter (1800) to pass through introducer sheath (1801), the lumen diameter of introducer sheath (1801) is at least the sum of the outer diameters of first branch stent (1804) and second branch stent (1807). It is advantageous to minimize the diameter of the introducer sheath to facilitate percutaneous delivery of the bifurcated stent through narrow access vessels.

FIG. 18B shows a cross-sectional view of another embodiment of catheter (1810) as described herein in the parallel configuration placed into introducer sheath (1811). The cross sections of proximal shaft (1812), first balloon (1813), first branch stent (1814), distal shaft (1815), second balloon (1816), and second branch stent (1817) are oval in shape. The oval shapes of catheter components (1812-1817) result in a smaller outer diameter of catheter (1810) in FIG. 18B compared to catheter (1800) in FIG. 18A and are configured to allow the placement of catheter (1810) through a smaller diameter introducer sheath (1811) in FIG. 18B compared to introducer sheath (1801) in FIG. 18A. In some embodiments, the catheter components can have D-shaped cross-sections. In other embodiments, the components can have any non-circular cross-section that results in a reduction of the outer diameter of the catheter.

Figure 19:
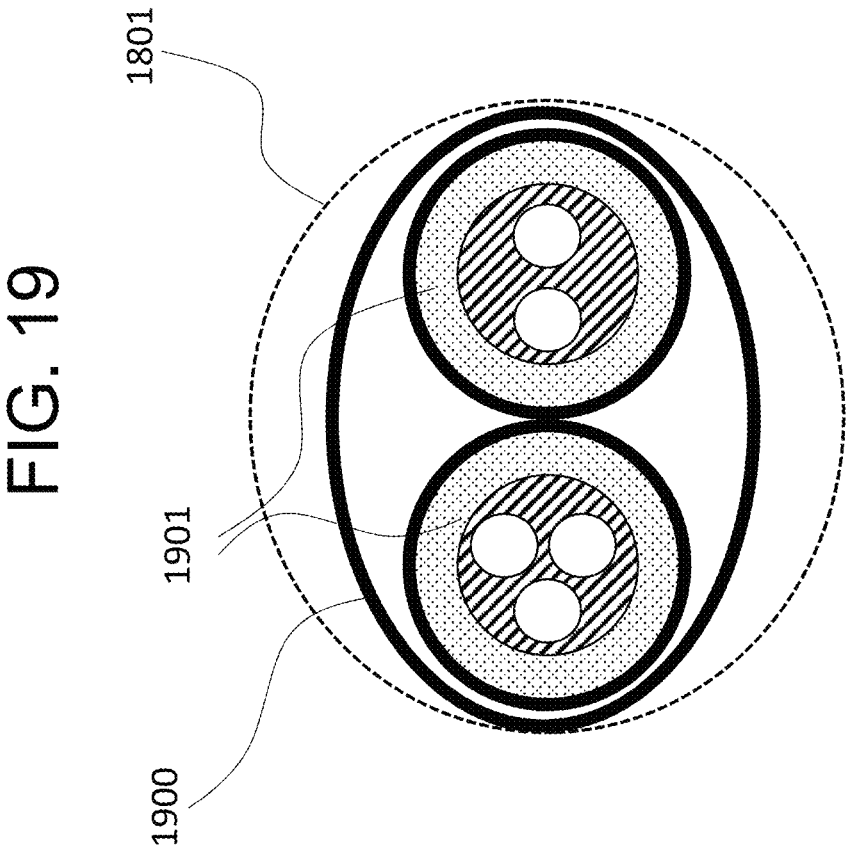
FIG. 19 illustrates the cross-sectional view of another embodiment of a bifurcated stent system described herein.

FIG. 19 shows another embodiment of an introducer sheath described herein. Catheter (1901) can be identical to catheter (1800) shown in FIG. 18A. Introducer sheath (1900) can include an oval cross-sectional shape to accommodate introducer sheath (1801). The shape of circular introducer sheath (1801) from FIG. 18A is indicated by the dashed line. The oval shape reduces the circumference of introducer sheath (1900) and facilitates the passage of introducer sheath (1900) into smaller blood vessels.

Figure 20A:
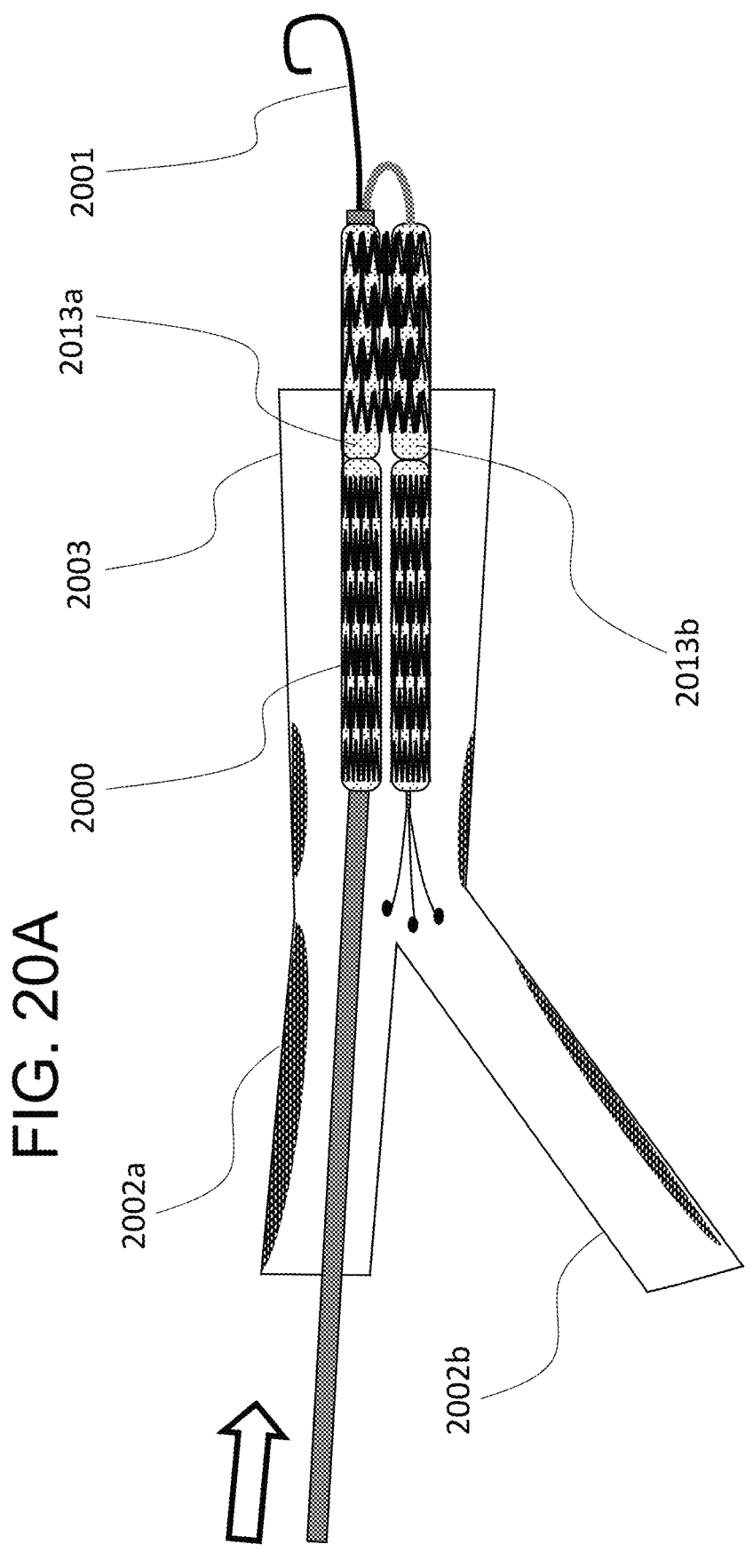
FIG. 20A illustrates advancing a bifurcated stent system over a guidewire through an ipsi-lateral iliac artery into an infra-renal aorta.

FIGS. 20A-20G illustrate some steps for placing a bifurcated stent into the aorto-iliac bifurcation. The illustrated steps can utilize an embodiment of the bifurcated stent system as depicted in FIGS. 15A-B. The illustrated steps can utilize another embodiment of the bifurcated stent system. Methods of accessing the peripheral arteries for catheter delivery of an implant are well described in the clinical literature and are not the subject of this invention. Percutaneous access is typically obtained from the femoral artery. A guidewire is then advanced from the femoral access vessel to the aorta. FIG. 20A illustrates the step of advancing bifurcated stent system (2000) over guidewire (2001) through ipsi-lateral iliac artery (2002a) into infra-renal aorta (2003). First balloon (2013a) and second balloon (2013b) are in a substantially parallel configuration. Bifurcated stent system (2000) can be advanced through right iliac artery (2002a) as shown in FIG. 20A. In other embodiments, bifurcated stent system (2000) can be advanced through left iliac artery (2002b). In some embodiments, bifurcated system (2000) can be advanced through an introducer sheath or guide catheter.

Figure 20B:
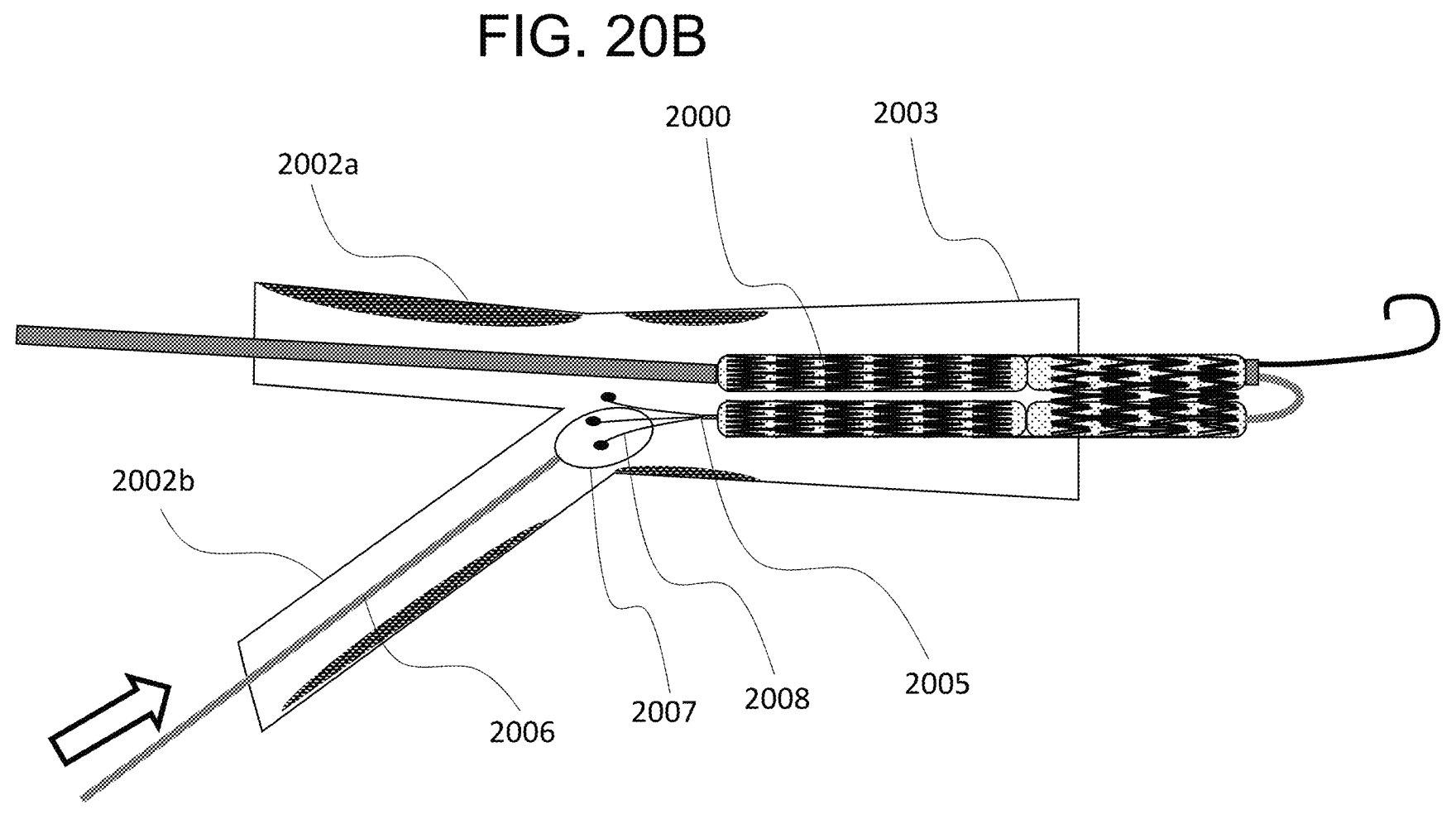
Figure 20C:
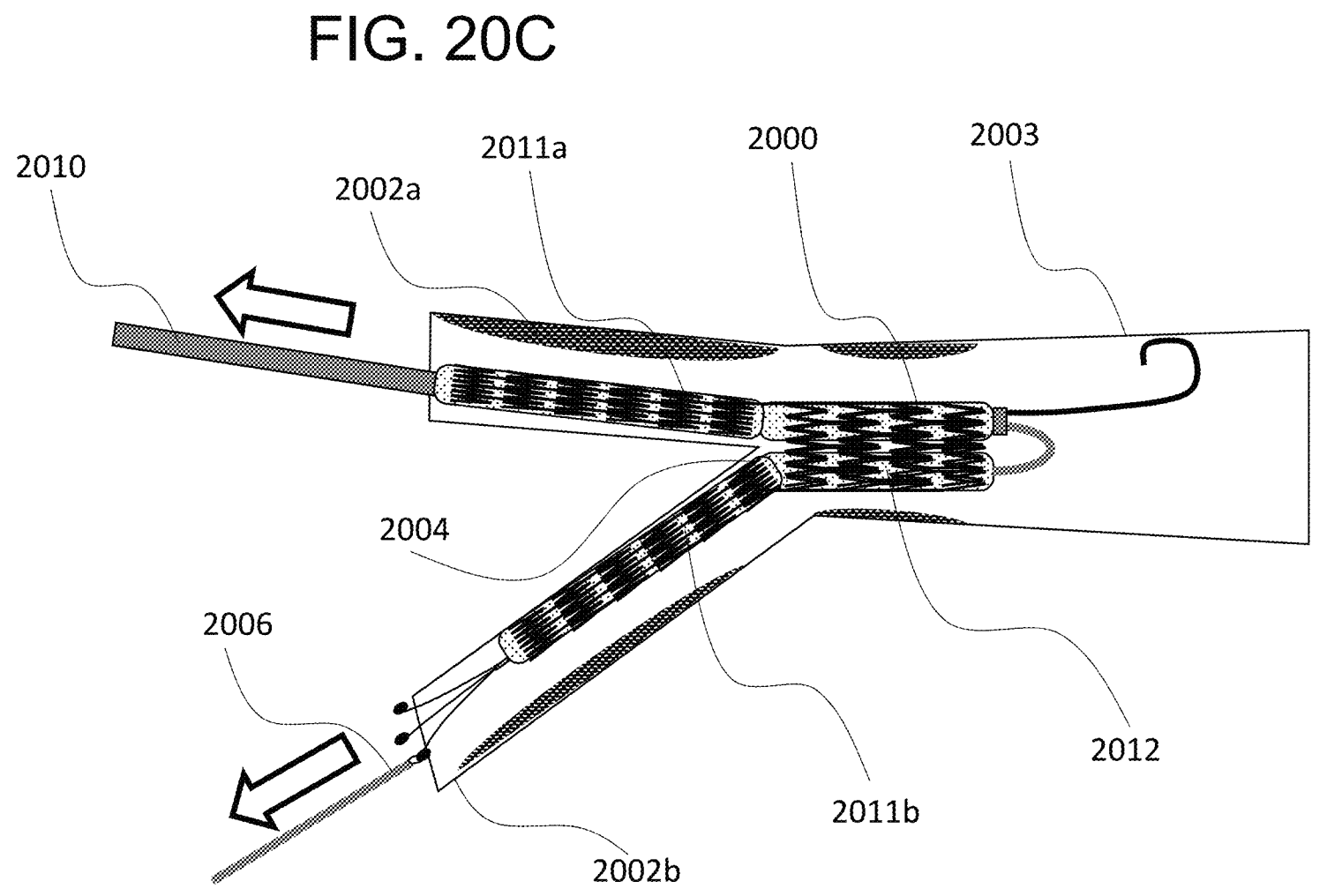

FIG. 20B illustrates the step of capturing the distal end of distal shaft (2005) with intravascular snare (2006). Snare (2006) is advanced from an access vessel on the contra-lateral side through contra-lateral iliac artery (2002b). Under fluoroscopic guidance, snare loop (2007) is placed over the distal end of distal shaft (2005). Snaring mechanism (2008) can be attached to the distal end of distal shaft (2005) to facilitate the snaring procedure. Snare loop (2007) is then closed over the distal end of distal shaft (2005) or snaring mechanism (2008). FIG. 20C illustrates the retraction of bifurcated stent system (2000) onto aorto-iliac bifurcation (2004). Catheter (2010) and snare (2006) are simultaneously moved proximally to place ipsi-lateral branch stent (2011a) into ipsi-lateral iliac artery (2002a), contra-lateral branch stent (2011 *b*) into contra-lateral iliac artery (2002*b*), and main body stent (2012) into the proximal segment of infra-renal aorta (2003).

Figure 20D:
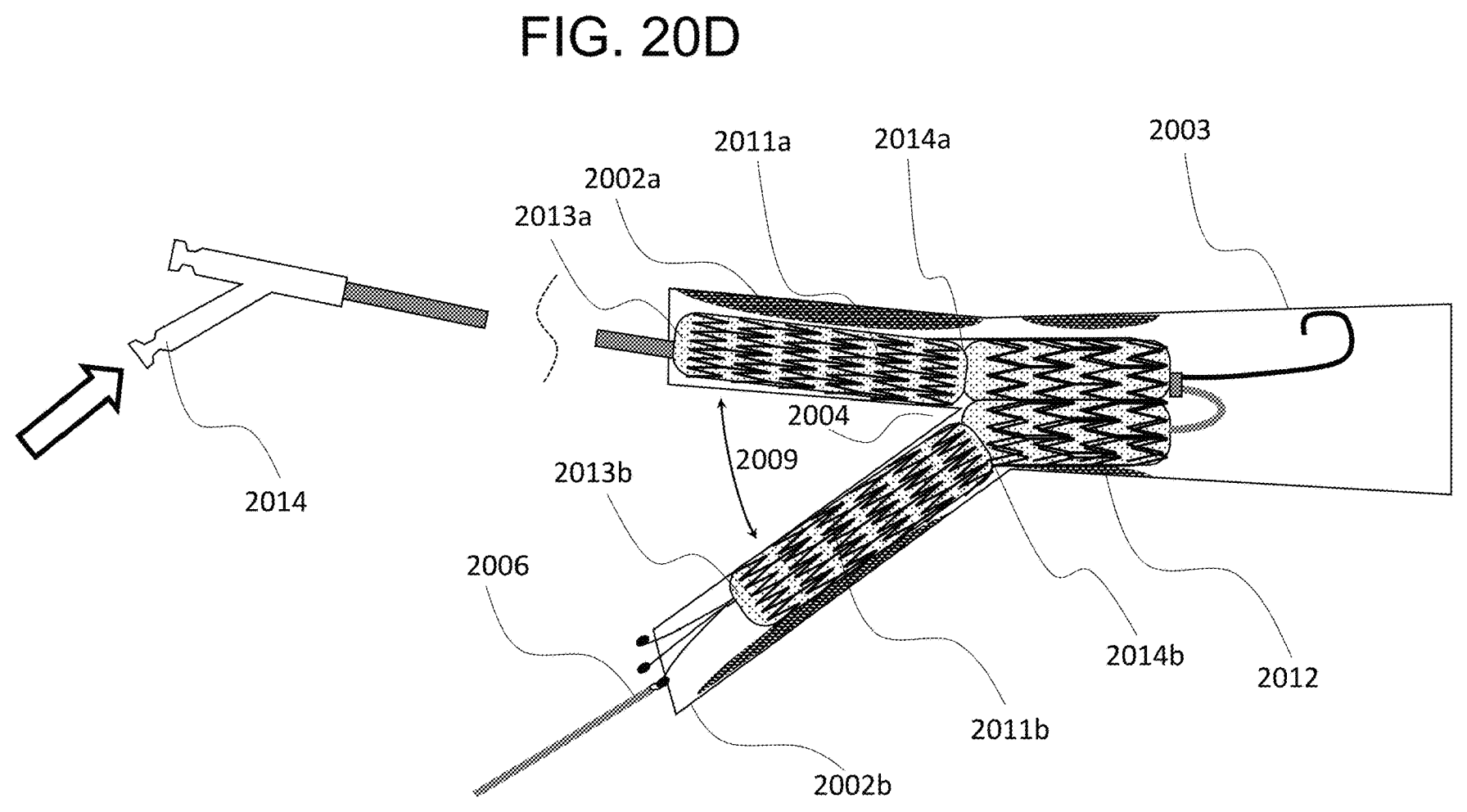

FIG. 20D illustrates the step of inflating balloons (2013*a*-*b*). Fluid is injected into inflation port (2014). Inflation port (2014) is in fluid communication with first balloon (2013*a*) and second balloon (2013*b*). The injected fluid simultane-ously fills first balloon (2013*a*) and second balloon (2013*b*). First balloon (2013*a*) expands ipsi-lateral branch stent (2011*a*). Second balloon (2013*b*) expands contra-lateral branch stent (2011 *b*). Both balloons (2013*a*-*b*) expand main body stent (2012). The cross-sections of expanded ipsi-lateral branch stent (2011*a*) and expanded contralateral branch stent (2011*b*) are circular. The cross-section of expanded main body stent (2012) is oval. Iliac arteries (2002*a*-*b*) branch at an angle from infra-renal aorta (2003). Angle (2009) between iliac arteries (2002*a*-*b*) can be between about 20 degrees to about 120 degrees. In some embodiments, the angle between the iliac arteries can be about 20 degrees, about 30 degrees, about 40 degrees, about 50 degrees, about 60 degrees, about 70 degrees, about 80 degrees, about 90 degrees, about 100 degrees, about 110 degrees, or about 120 degrees. Waists (2014*a*-*b*) in balloons (2013*a*-*b*) are designed to increase the bending flexibility of balloons (2013*a*-*b*) at the location of aorto-iliac bifurcation (2004) and to minimize cross-over of balloons (2013*a*-*b*) in infra-renal aorta (2003).

Figure 20E:
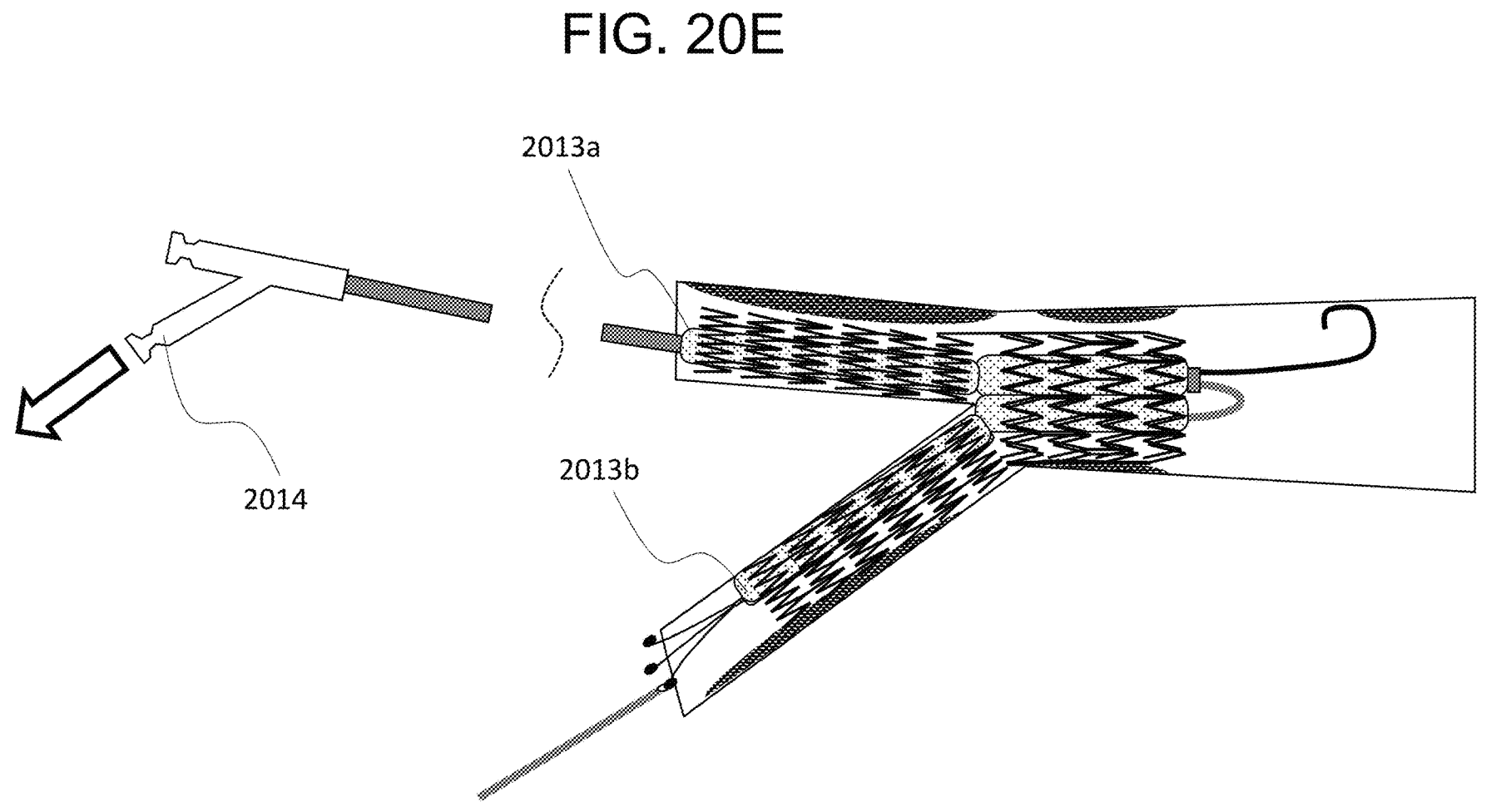
Figure 20F:
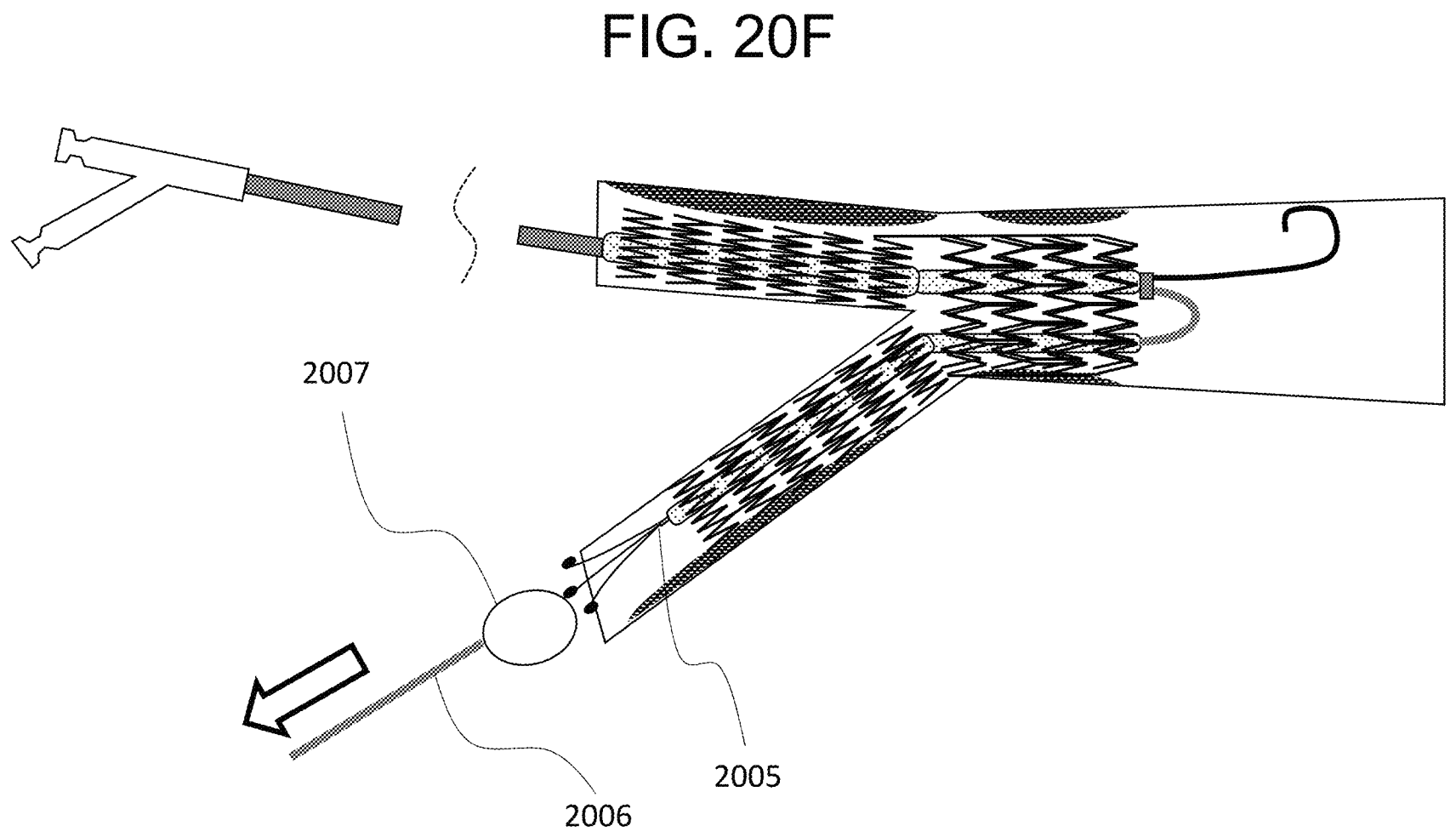
Figure 20G:
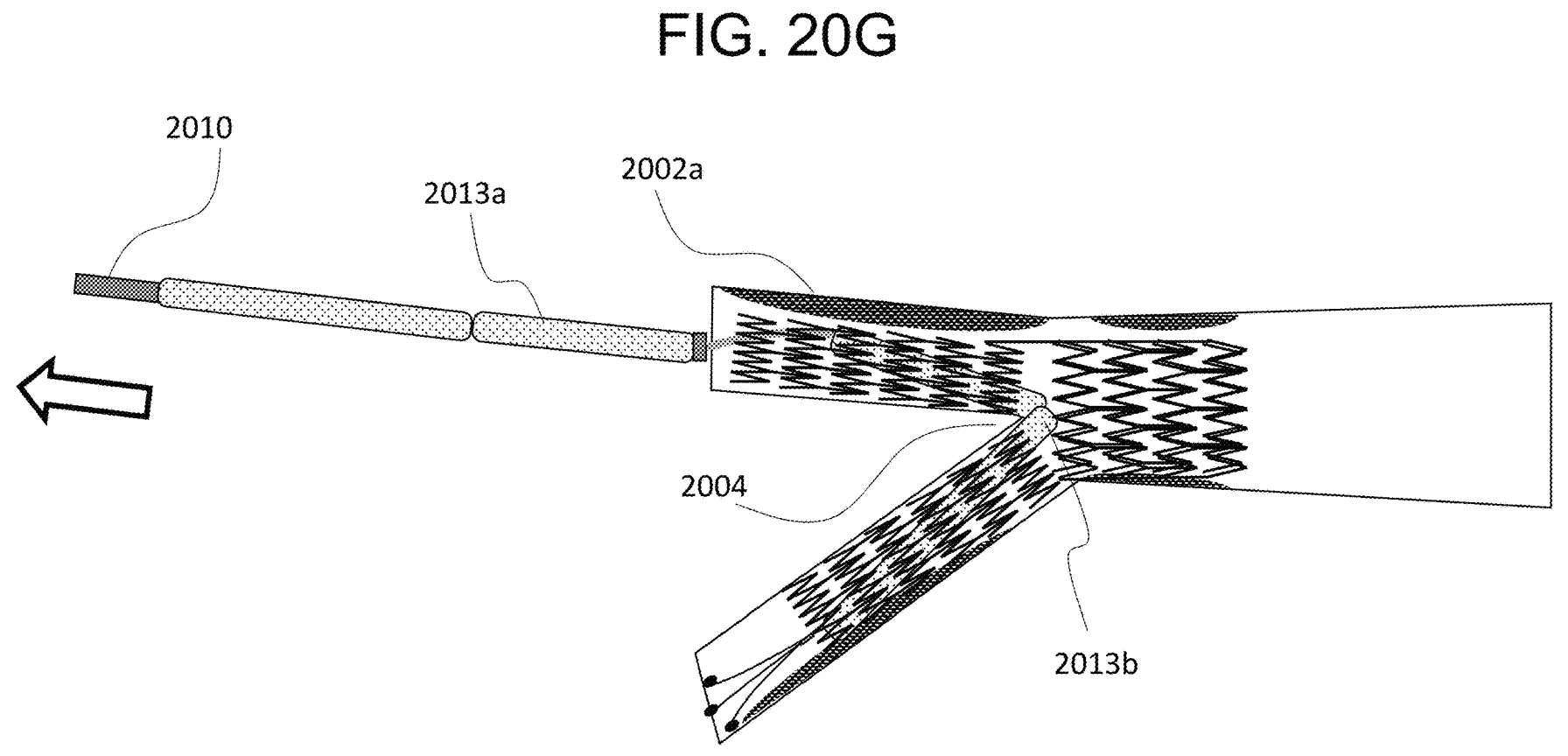
Figure 20H:
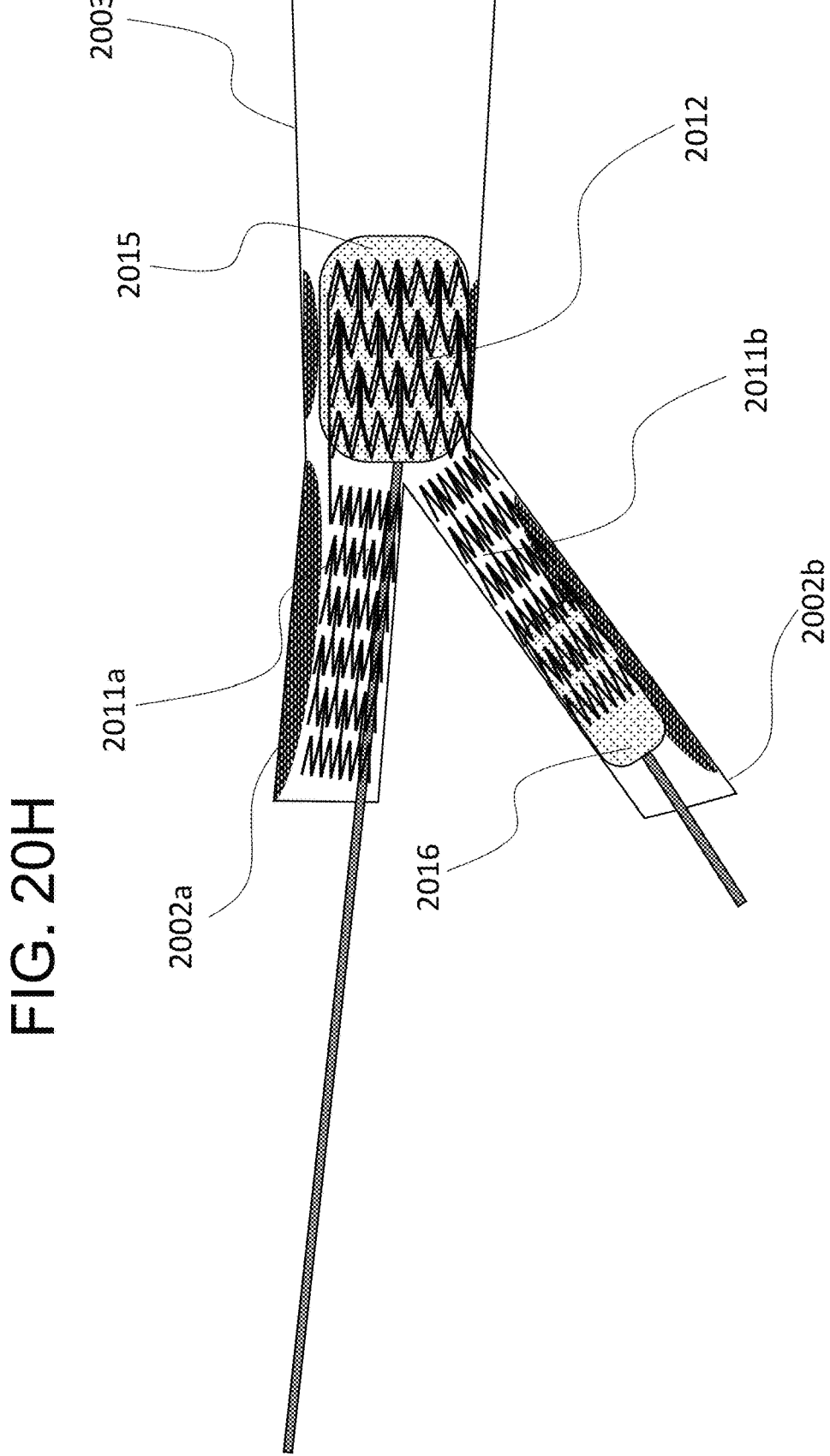
FIG. 20H illustrates post-ballooning branch stent with a first percutaneous transluminal angioplasty balloon and a main-body.

FIG. 20E illustrates the deflation of balloons (2013*a*-*b*). The fluid is removed from balloons (2013*a*-*b*) and balloons (2013*a*-*b*) are collapsed by applying a negative pressure at inflation port (2014). FIG. 20F illustrates the step of releas-ing distal shaft (2005) from intravascular snare (2006). Snare loop (2007) is opened and snare (2006) is retracted proximally. FIG. 20G illustrates the step of withdrawing catheter (2010) from the arterial system. Retracting catheter (2010) proximally pulls second balloon (2013*b*) over aorto-iliac bifurcation (2004) into ipsi-lateral iliac artery (2002*a*). As catheter (2010) is being retracted through the ipsi-lateral blood vessels, first balloon (2013*a*) and second balloon (2013*b*) are in a substantially serial configuration. FIG. 20H illustrates the step of post-ballooning branch stents (2011*a*-*b*) with first percutaneous transluminal angioplasty (PTA) balloon (2016) and main-body stent (2012) with second PTA balloon (2015) to conform branch stents (2011*a*-*b*) to the walls of iliac arteries (2002*a*-*b*) and main body stent (2012) to the wall of infra-renal aorta (2003). Post-ballooning of main body stent (2012) changes the cross-section of main body stent (2012) from an oval shape into a circular shape.

Figure 21A:
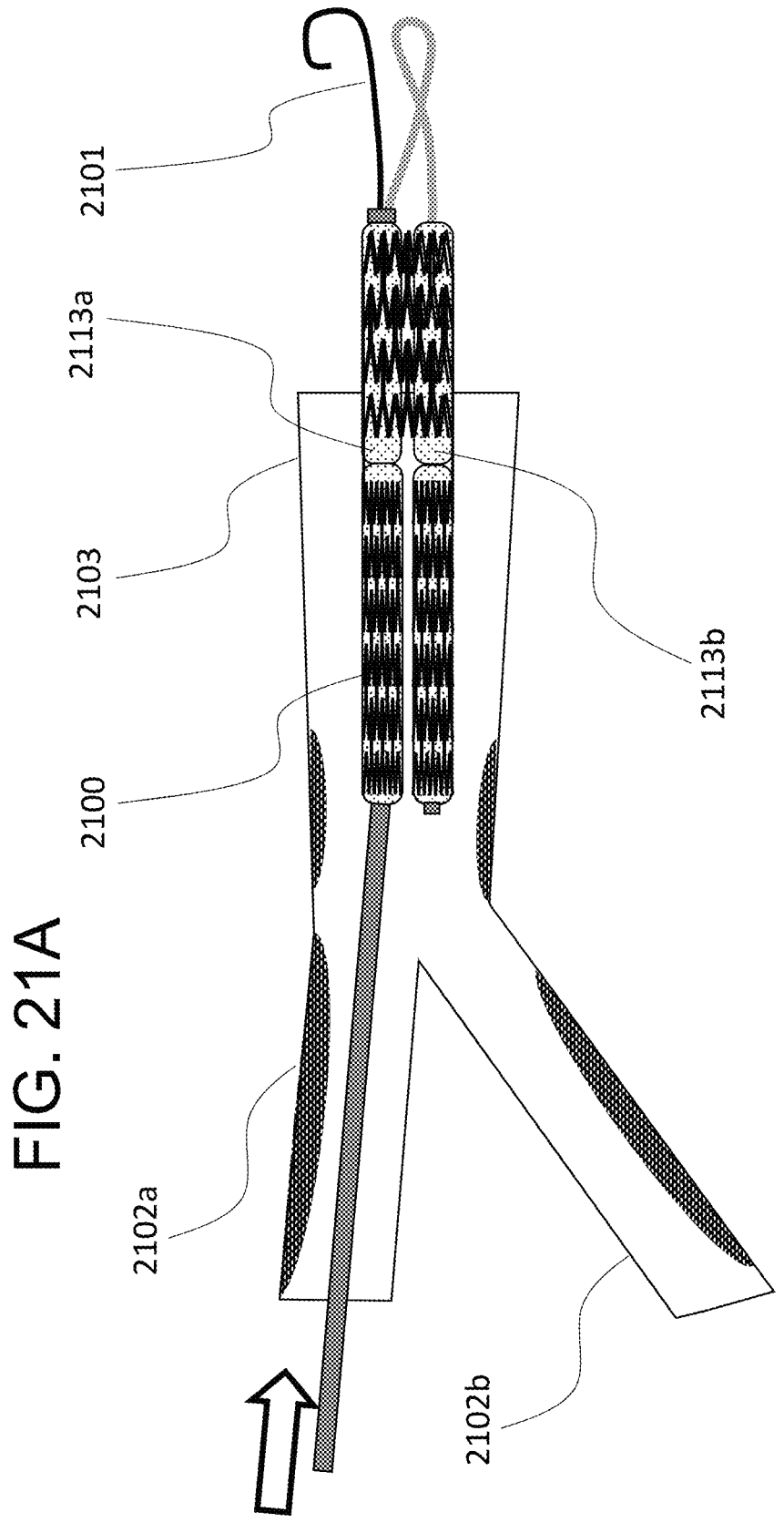
FIG. 21A illustrates advancing a bifurcated stent system over a first guidewire through a ipsi-lateral iliac artery into a infra-renal aorta.
Figure 21B:
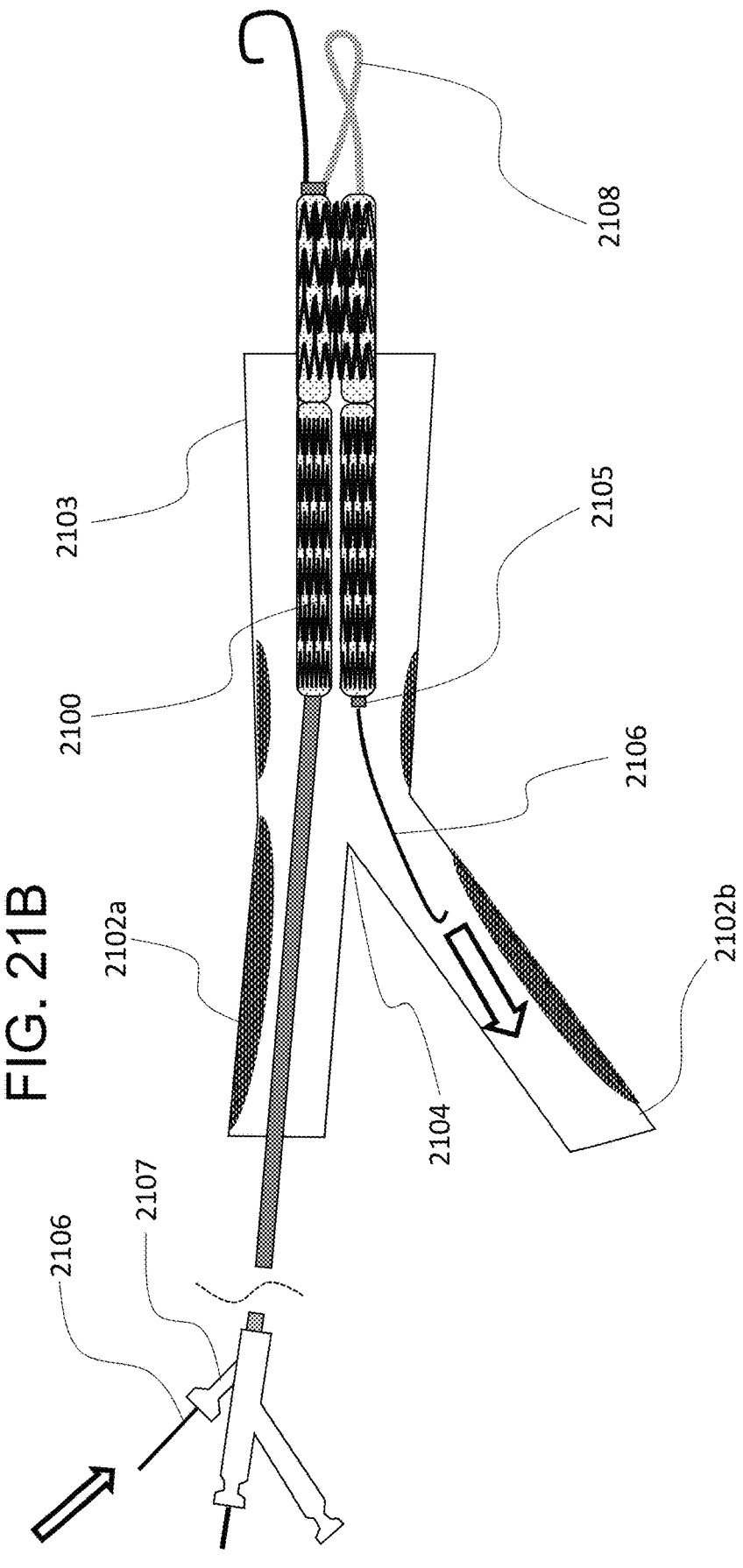
FIG. 21B illustrates placing a second guidewire into a contra-lateral iliac artery.
Figure 21C:
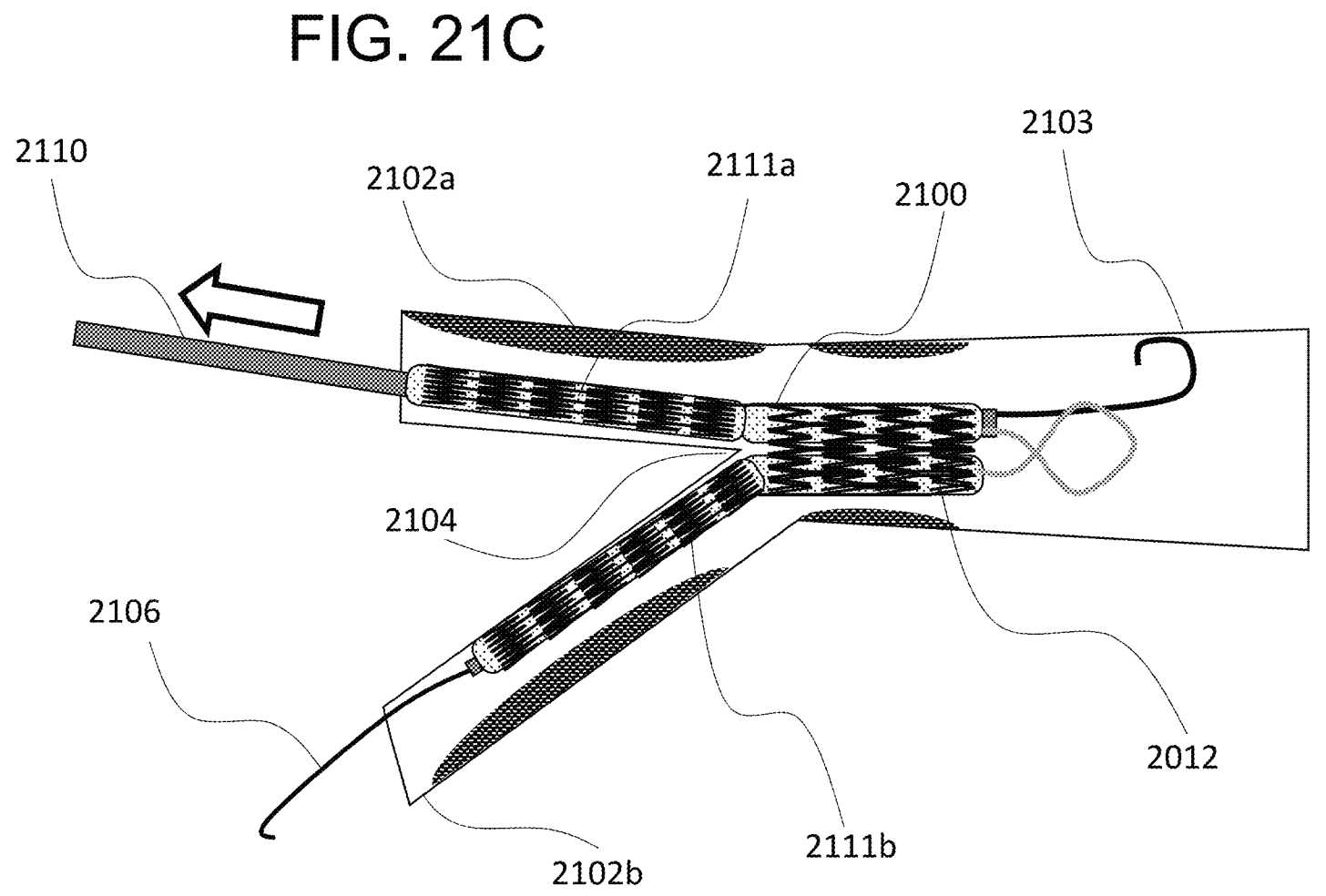
Figure 21D:
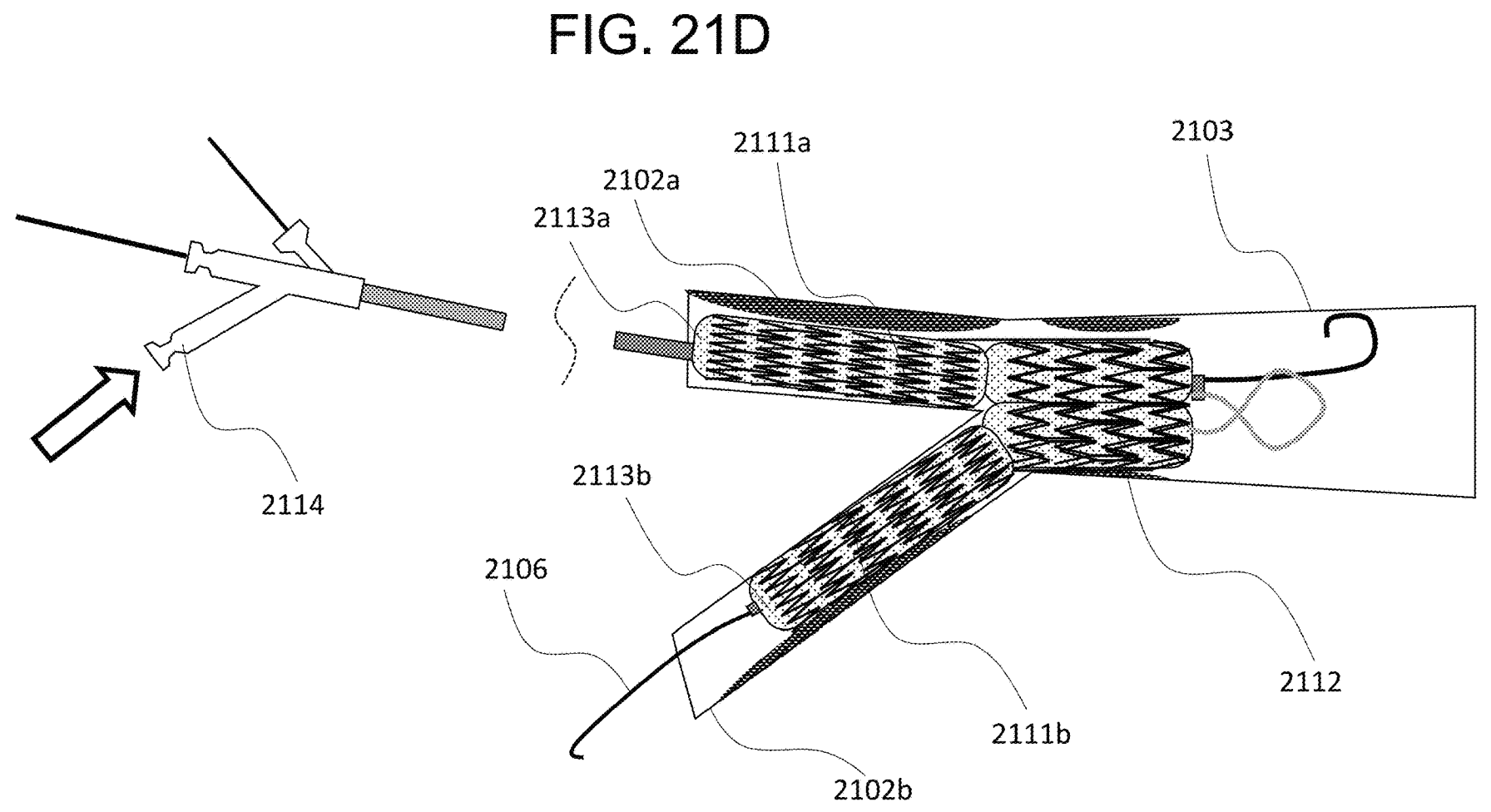
Figure 21E:
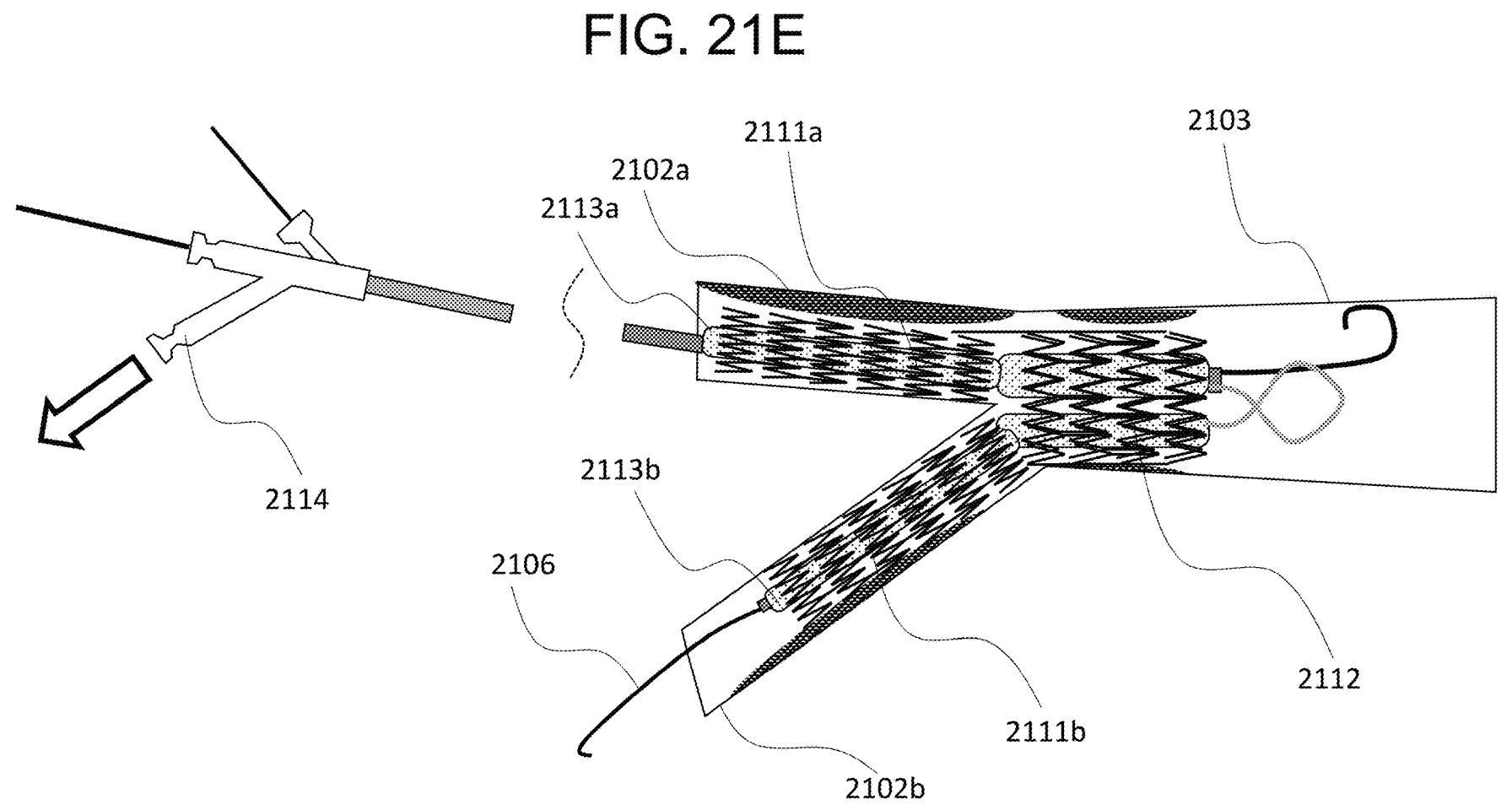
Figure 21F:
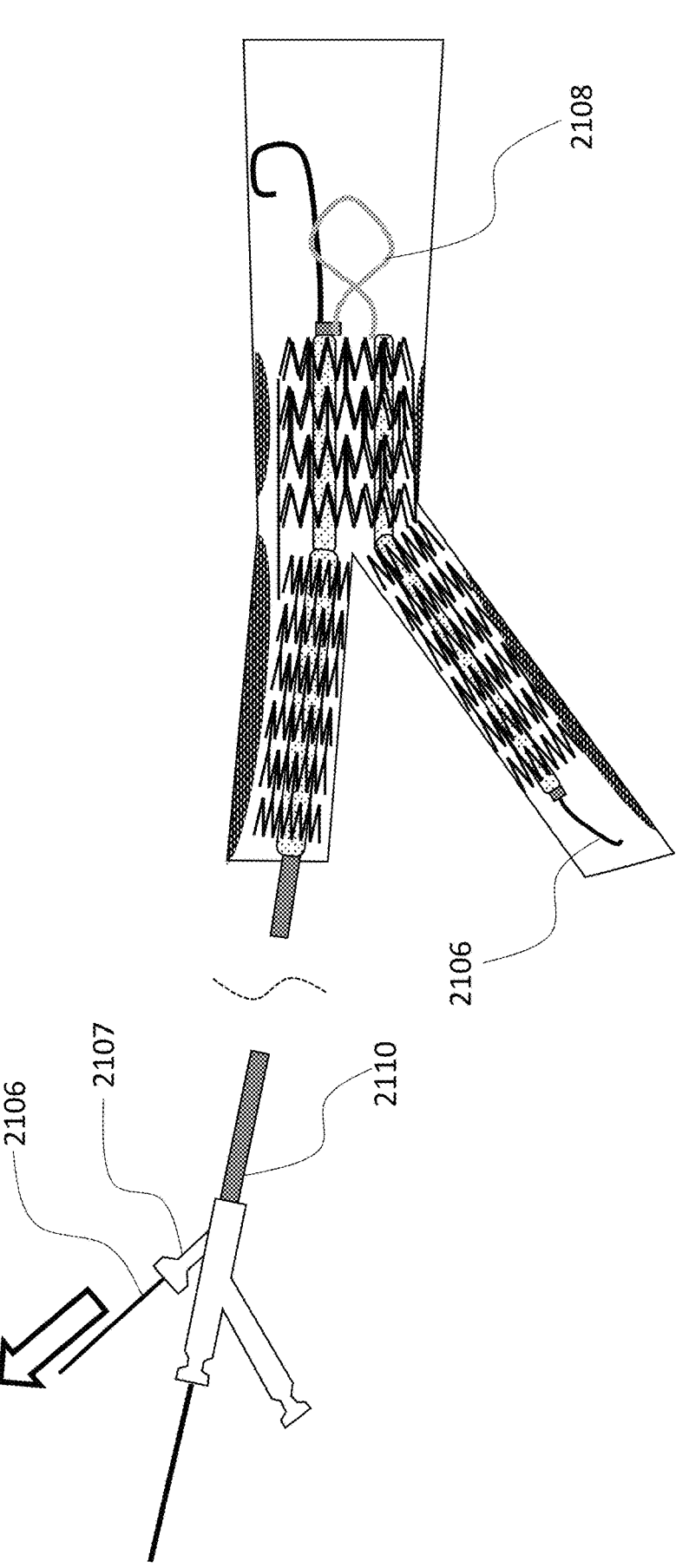
FIG. 21F illustrates retracting the second guidewire of FIG. 21B.

FIGS. 21A-G illustrate some steps for placing a bifur-cated stent into the aorto-iliac bifurcation utilizing an embodiment of the bifurcated stent system described in FIG. 17. The illustrated steps can utilize another embodiment of the bifurcated stent system. FIG. 21A illustrates the step of advancing bifurcated stent system (2100) over first guidewire (2101) through ipsi-lateral iliac artery (2102*a*) into infra-renal aorta (2103). First balloon (2113*a*) and second balloon (2113*b*) are in a substantially parallel con-figuration. Bifurcated system (2100) can be advanced through an introducer sheath or guide catheter. FIG. 21 B illustrates the step of placing second guidewire (2106) into contra-lateral iliac artery (2102*a*). Second guidewire (2106) is advanced from second guidewire port (2107) through the flexible shaft connector (2108) and through distal shaft (2105) into contra-lateral iliac artery (2102*b*). If needed, an intravascular snare can be used to snare second guidewire (2106) and advance it into contra-lateral iliac artery (2102*b*).

The large radius of curvature of the looped shaft connector (2108) is designed to reduce the forces required to advance second guidewire (2106) over aorto-iliac bifurcation (2104).

FIG. 21C illustrates the retraction of bifurcated stent system (2100) onto aorto-iliac bifurcation (2104). Catheter (2110) is moved proximally to place ipsi-lateral branch stent (2111*a*) into ipsi-lateral iliac artery (2102*a*). Second guidewire (2106) guides contra-lateral branch stent (2111*b*) into contra-lateral iliac artery (2102*b*). A potential advantage of the steps described in FIGS. 21 B-C over the steps described in FIGS. 20B-C is that the steps in FIGS. 21 B-C do not require cannulation of the contra-lateral iliac artery. FIG. 21 D illustrates the step of inflating balloons (2113*a*-*b*). Fluid is injected into inflation port (2114). Inflation port (2114) is in fluid communication with first balloon (2113*a*) and second balloon (2113*b*). The injected fluid simultane-ously fills first balloon (2113*a*) and second balloon (2113*b*). First balloon (2113*a*) expands ipsi-lateral branch stent (2111*a*). Second balloon (2113*b*) expands contra-lateral branch stent (2111*b*). Both balloons (2113*a*-*b*) expand main body stent (2112). The cross-sections of the expanded ipsi-lateral branch stent (2111*a*) and the expanded contra-lateral branch stent (2111 *b*) are circular. The cross-section of the expanded main body stent (2112) is oval. FIG. 21 E illus-trates the deflation of balloons (2113*a*-*b*). The fluid is removed from balloons (2113*a*-*b*) and balloons (2113*a*-*b*) are collapsed by applying a negative pressure at inflation port (2114). FIG. 21 F illustrates the step of retracting second guidewire (2106) from catheter (2110). Removing second guidewire (2106) increases the flexibility of catheter (2110) in particular the flexibility of shaft connector (2108) for removal of catheter (2110) from the arterial system. In other embodiments, second guidewire (2106) can remain in place in contra-lateral iliac artery (2102*b*) to facilitate addi-tional percutaneous procedures in contra-lateral iliac artery (2102*b*) or other contra-lateral arteries.

Figure 21G:
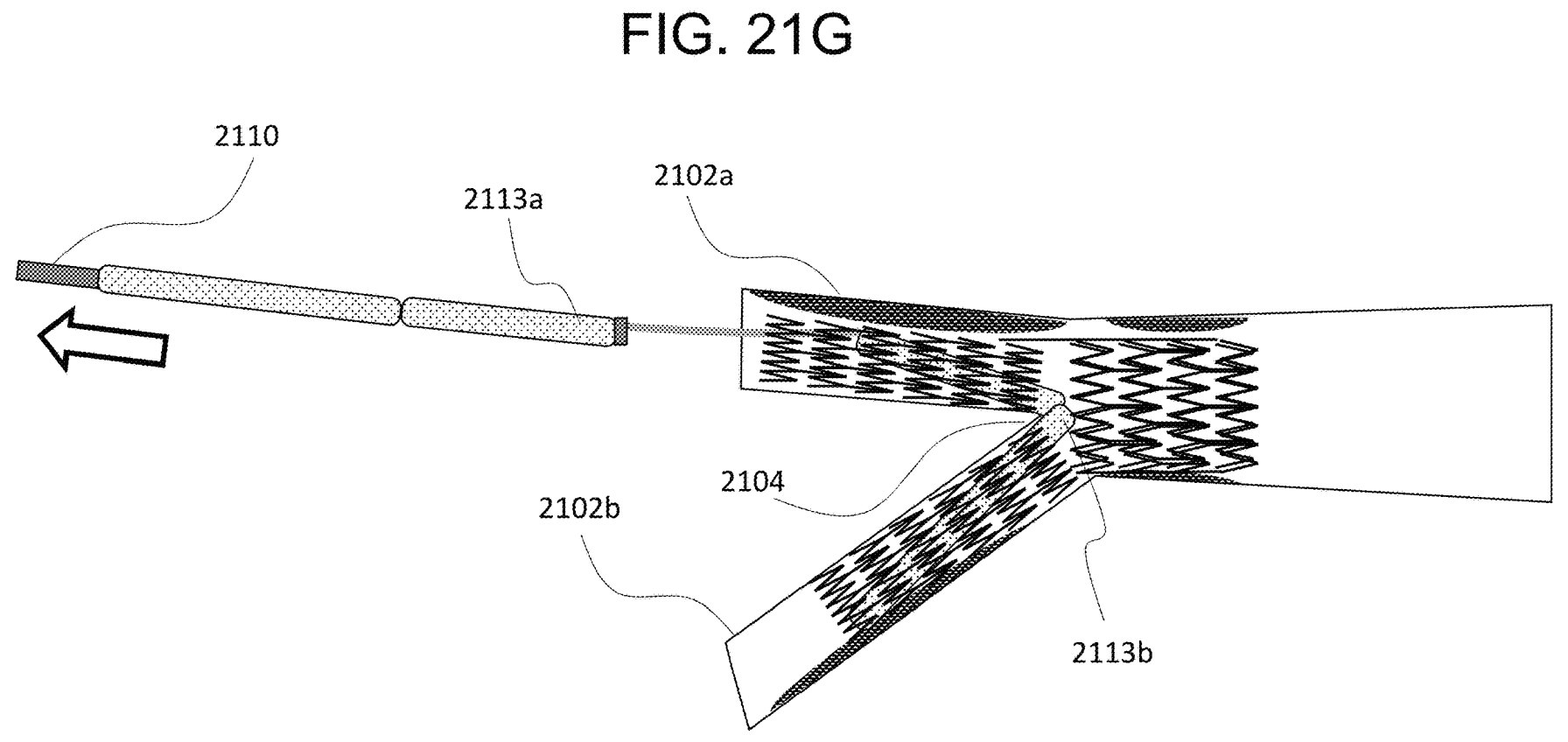
Figure 21H:
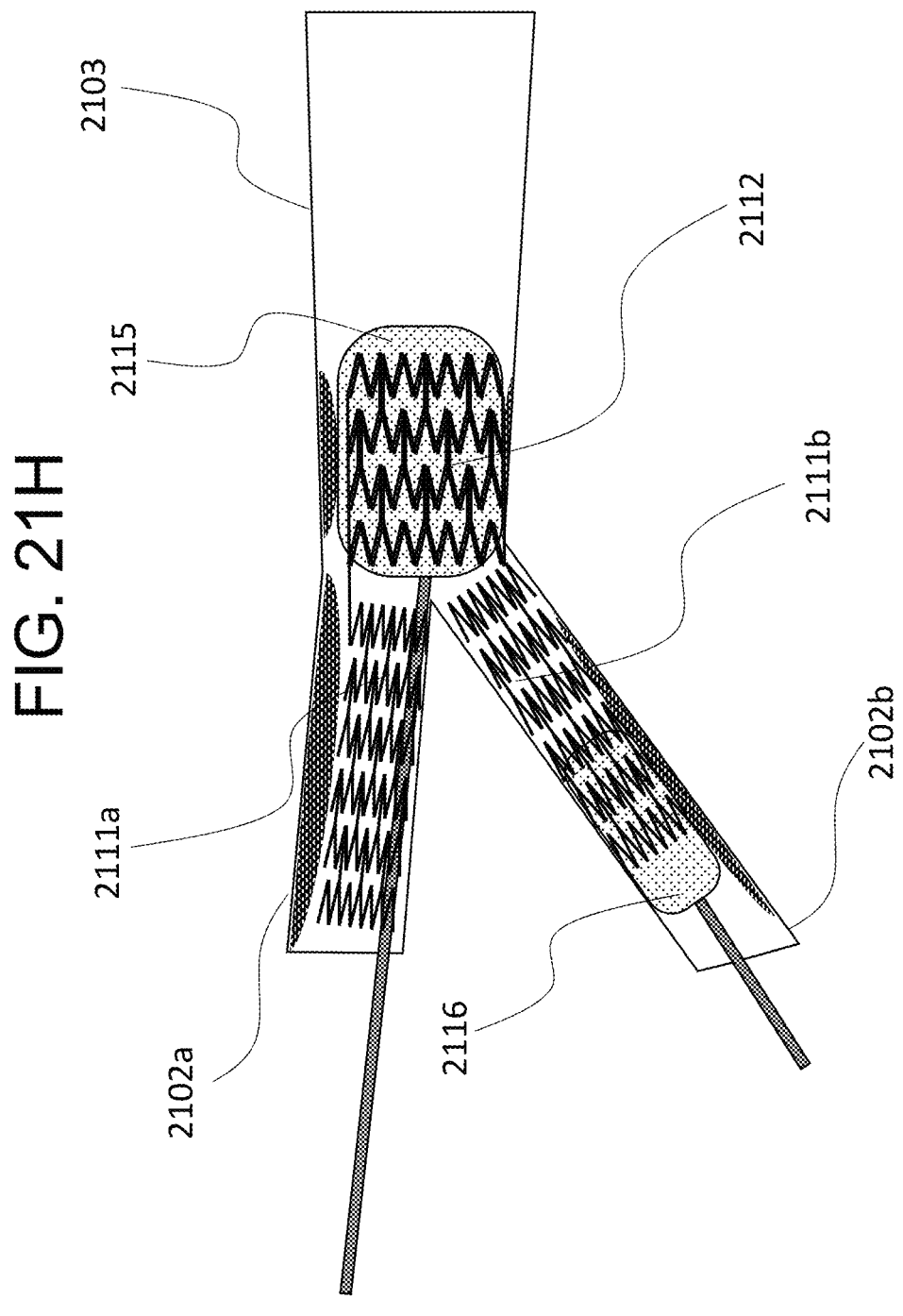
FIG. 21H illustrates post-ballooning branch stents of a bifurcated stent of the bifurcated stent system of FIG. 21A with a first percutaneous transluminal angioplasty balloon and a main body stent of the bifurcated stent with a second percutaneous transluminal angioplasty balloon to conform the branch stents to the wall of the iliac arteries and the main body stent to the wall of the infra-renal aorta.

FIG. 21G illustrates the step of withdrawing catheter (2110) from the arterial system. Retracting catheter (2110) proximally pulls second balloon (2113*b*) over the aorto-iliac bifurcation into ipsi-lateral iliac artery (2102*a*). As catheter (2110) is being retracted through the ipsi-lateral blood vessels, first balloon (2113*a*) and second balloon (2113*b*) are in a substantially serial configuration. FIG. 21H illustrates the step of post-ballooning branch stents (2111*a*-*b*) with first percutaneous transluminal angioplasty (PTA) balloon (2116) and main-body stent (2112) with second PTA balloon (2115) to conform branch stents (2111*a*-*b*) to the wall of iliac arteries (2102*a*-*b*) and main body stent (2112) to the wall of infra-renal aorta (2103). Post-ballooning of main body stent (2112) changes the cross-section of main body stent (2112) from an oval shape into a circular shape.

In some embodiments, a system for treating a diseased bifurcating blood vessel comprises: a bifurcated stent, a catheter for delivering the bifurcated stent into the bifurcated blood vessel, the catheter comprising a first balloon and a second balloon; wherein in a first configuration the first balloon and the second balloon are substantially arranged in series and in a second configuration the first balloon and the second balloon are substantially arranged in parallel.

In other embodiments, a catheter for delivering a bifur-cated stent into a diseased bifurcating blood vessel com-prises: a catheter shaft, a first balloon and a second balloon mounted onto the catheter shaft; the catheter having a first configuration with the first balloon and the second balloon substantially arranged in series; the catheter having a second configuration with the first balloon and the second balloon substantially arranged in parallel.

In some embodiments, a system for treating a diseased bifurcating blood vessel comprises: a bifurcated stent having a main body stent and a first and a second branch stent, a catheter for delivering the bifurcated stent into the bifurcating blood vessel, the catheter including a first balloon and a second balloon; wherein the first branch stent is mounted onto the first balloon, the second branch stent is mounted onto the second balloon, and the main body stent is mounted onto the first balloon and the second balloon.

In other embodiments, a catheter for delivering a bifurcated stent into a bifurcating blood vessel comprises: a shaft, a first balloon and a second balloon mounted onto the shaft and a flexible shaft segment connecting the first balloon and the second balloon; wherein in a first configuration the flexible shaft segment forms a loop and in a second configuration the flexible shaft segment is substantially straight.

In some embodiments, a method for treating a diseased bifurcating blood vessel having a main vessel and two branch vessels comprises: mounting a bifurcated stent having a main body stent and a first and a second branch stent onto a catheter having a first balloon and a second balloon; placing the bifurcated stent into the bifurcating blood vessel; expanding the first branch stent by inflating the first balloon, expanding the second branch stent by inflating the second balloon, and expanding the main body stent by inflating the first balloon and the second balloon.

In other embodiments, a method for treating a diseased bifurcating blood vessel including a main vessel and two branch vessels comprising: mounting a bifurcated stent including a main body stent and a first and a second branch stent onto a catheter including a first balloon and a second balloon; advancing the catheter through a first branch vessel to the bifurcation with the first balloon and second balloon being in a substantially parallel configuration; deploying the bifurcated stent by simultaneously inflating the first balloon and the second balloon; retracting the catheter through the first branch vessel with the first balloon and second balloon being in a substantially serial configuration.

In some embodiments, a method for treating a diseased bifurcating blood vessel including a main vessel and two branch vessels comprises: mounting a bifurcated stent having a main body stent and a first and second branch stent onto a catheter including a first balloon and a second balloon; advancing the catheter through the first branch vessel to the bifurcating blood vessel; positioning a first end of the first balloon into the first branch vessel; positioning a second end of the first balloon into the main vessel; positioning a first end of the second balloon into the second branch vessel; positioning a second end of the second balloon into the main vessel.

While the above is a complete description of the preferred embodiments of the invention, various alternatives, modifications, and equivalents may be used. The various features of the embodiments disclosed herein may be combined or substituted with one another. Therefore, the above description should not be taken as limiting in scope of the invention which is defined by the appended claims.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

US 12,685,653 B2

17

The invention claimed is:

1. A system for treating a diseased bifurcating blood vessel, the system comprising:
   a bifurcated stent comprising a main body stent, a first branch stent, and a second branch stent;
   a catheter for delivering the bifurcated stent into the diseased bifurcated blood vessel, the catheter comprising:
      a first balloon and a second balloon arranged substantially in parallel; and
      a looped guidewire lumen that passes a guidewire through the first balloon and second balloon;
   wherein the first branch stent is crimped onto the first balloon, the second branch stent is crimped onto the second balloon, and the main body stent is crimped onto the first balloon and the second balloon.

2. The system of claim 1, wherein the first balloon and the second balloon comprise a waist positioned between the branch stents and the main body stent.

3. The system of claim 1, wherein the catheter further comprises an inflation port that is in fluid communications with the first and second balloon.

4. The system of claim 1, wherein the first and the second branch stents are crimped into an oval cross-section and the main body stent is crimped into a circular cross-section.

5. The system of claim 1, wherein the bifurcated stent comprises a cover of a biocompatible material.

6. The system of claim 5, wherein a distal segment of the main body stent is not covered with the biocompatible material.

7. The system of claim 5, wherein the cover of a distal segment of the main body stent comprises an opening or a cutout.

8. A method for treating a diseased bifurcating blood vessel including a main vessel and two branch vessels, the method comprising:
   mounting a bifurcated stent including a main body stent and a first branch stent and a second branch stent onto a catheter having a first balloon and a second balloon;
   advancing the bifurcated stent through a first branch vessel toward a bifurcation point of the diseased bifurcating blood vessel;
   placing the bifurcated stent into the bifurcating blood vessel;
   expanding the first branch stent into the first branch vessel by inflating the first balloon;
   expanding the second branch stent into a second branch vessel by inflating the second balloon; and
   expanding the main body stent into the main vessel by simultaneously inflating the first balloon and the second balloon.

9. The method of claim 8, wherein the branch stents are expanded from an oval cross-section into a circular cross-section.

10. The method of claim 8, wherein the main body stent is expanded from a circular cross-section into an oval cross-section.

11. The method of claim 10, further comprising:
   removing the catheter;
   advancing a first percutaneous transluminal balloon to the main body stent; and
   inflating the first percutaneous transluminal balloon to expand the main body stent from the oval cross-section to a circular cross-section.

12. The method of claim 8, wherein the first and second balloons are arranged in a substantially parallel configuration when inserted into the bifurcated blood vessel.

13. The method of claim 8, wherein the catheter further comprises a looped guidewire lumen that passes a guidewire through the first balloon and second balloon.

14. A balloon catheter for delivering a bifurcated stent into a bifurcated blood vessel, the balloon catheter comprising:
   a proximal hub;
   a shaft;
   a first balloon connected to the shaft;
   a second balloon in fluid communication with the first balloon, wherein the first and second balloons are arranged in a substantially parallel configuration when inserted into the bifurcated blood vessel;
   an inflation port at the proximal hub in fluid communication with the first balloon and second balloon;
   a first guidewire lumen extending through the proximal hub, the shaft, and the first balloon; and
   a second guidewire lumen extending through the proximal hub, the first balloon, and the second balloon.

15. The balloon catheter of claim 14, wherein the first and second balloons are cylindrical in shape and have a narrowing in the midsection.

16. The balloon catheter of claim 14, wherein the first and second balloons are arranged in a expandable configuration when inflated in the bifurcated blood vessel.

17. The balloon catheter of claim 16, wherein a distal end of the second guidewire comprises a snare.

18. The balloon catheter of claim 17, wherein the snare comprises a plurality of antenna-like structures.

19. The balloon catheter of claim 16, further comprising a shaft connector that couples the first balloon to the second balloon, wherein the shaft connector is reinforced by a metal coil, and wherein an inflation lumen extends through the proximal hub, the shaft, the first balloon, the shaft connector, and wherein the second guidewire lumen extends through the shaft connector.

20. The balloon catheter of claim 14, wherein the first and second balloons are arranged in series when removed from the bifurcated blood vessel.

* * * * *